US009980664B2

(12) United States Patent
Fernando et al.

(10) Patent No.: US 9,980,664 B2
(45) Date of Patent: May 29, 2018

(54) BIOLOGICAL SIGNAL MEASUREMENT SYSTEM, APPARATUS, METHOD, AND COMPUTER PROGRAM THEREOF

(71) Applicant: Panasonic Intellectual Property Management Co., Ltd., Osaka (JP)

(72) Inventors: Jeffry Bonar Fernando, Osaka (JP); Koji Morikawa, Kyoto (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 454 days.

(21) Appl. No.: 14/618,520

(22) Filed: Feb. 10, 2015

(65) Prior Publication Data
US 2015/0150485 A1    Jun. 4, 2015

Related U.S. Application Data

(63) Continuation of application No. PCT/JP2014/000587, filed on Feb. 4, 2014.

(30) Foreign Application Priority Data

Mar. 22, 2013  (JP) .................................. 2013-060214

(51) Int. Cl.
*A61B 5/08*    (2006.01)
*A61B 5/0452*   (2006.01)
(Continued)

(52) U.S. Cl.
CPC .......... *A61B 5/0809* (2013.01); *A61B 5/0452* (2013.01); *A61B 5/053* (2013.01);
(Continued)

(58) Field of Classification Search
USPC ......................................................... 600/484
See application file for complete search history.

(56) References Cited

U.S. PATENT DOCUMENTS 3,433,217 A  *  3/1969  Rieke .................. A61B 5/0809
                                                                600/536
6,537,228 B1    3/2003  Lambert
(Continued)

FOREIGN PATENT DOCUMENTS

JP          2820169 B2    8/1998
JP        11-253414 A     9/1999
(Continued)

OTHER PUBLICATIONS

International Search Report for corresponding International Application No. PCT/JP2014/000587 dated May 13, 2014.
(Continued)

*Primary Examiner* — Christian Jang
*Assistant Examiner* — Mitchell E Alter
(74) *Attorney, Agent, or Firm* — Renner, Otto, Boisselle & Sklar, LLP

(57) ABSTRACT

A biological information measurement system includes: a plurality of electrodes; a current source connected to the plurality of electrodes to supply a current thereto; a measurement unit for measuring impedance from a potential difference between the plurality of electrodes; a detector for detecting values of specific peaks from chronological data of the impedance; an envelope generator for generating an envelope of values of the specific peaks; and an output unit for outputting information of the envelope as biological information.

20 Claims, 34 Drawing Sheets

(51) Int. Cl.
   *A61B 5/053* (2006.01)
   *A61B 5/091* (2006.01)
   *A61B 5/00* (2006.01)

(52) U.S. Cl.
   CPC .......... *A61B 5/0531* (2013.01); *A61B 5/0816* (2013.01); *A61B 5/091* (2013.01); *A61B 5/7278* (2013.01)

(56) References Cited

U.S. PATENT DOCUMENTS

| | | | |
|---|---|---|---|
| 2001/0008953 A1 | 7/2001 | Honda et al. | |
| 2008/0183098 A1* | 7/2008 | Denison | A61B 5/0002 600/547 |
| 2010/0217133 A1* | 8/2010 | Nilsen | A61B 5/0205 600/484 |
| 2010/0312075 A1* | 12/2010 | McGonigle | A61B 5/0816 600/301 |
| 2014/0073863 A1* | 3/2014 | Engelbrecht | A61B 5/7203 600/301 |

FOREIGN PATENT DOCUMENTS

| | | | |
|---|---|---|---|
| JP | H11253414 | * | 9/1999 |
| JP | 2001-190510 | A | 7/2001 |
| JP | 2002-518077 | T | 6/2002 |
| JP | 3735774 | B2 | 11/2005 |
| JP | 2014-050626 | A | 3/2014 |

OTHER PUBLICATIONS

Sky McKinley et al.; "Cubic Spline Interpolation", Math 45: Linear Algebra; 1998.

Yoshifumi Yasuda et.al.; "Modified thoracic impedance plethysmography to monitor sleep apnea syndromes";.Sleep Medicine; vol. 6; pp. 215-224 (2005) (cited in [0011] of the specification).

Ciara O'Brien et al.; "A comparison of algorithms for estimation of a respiratory signal from the surface electrocardiogram";.Computers in Biology and Medicine; vol. 37; Issue 3, pp. 305-314 (2007) (cited in [0013] of the specification).

* cited by examiner

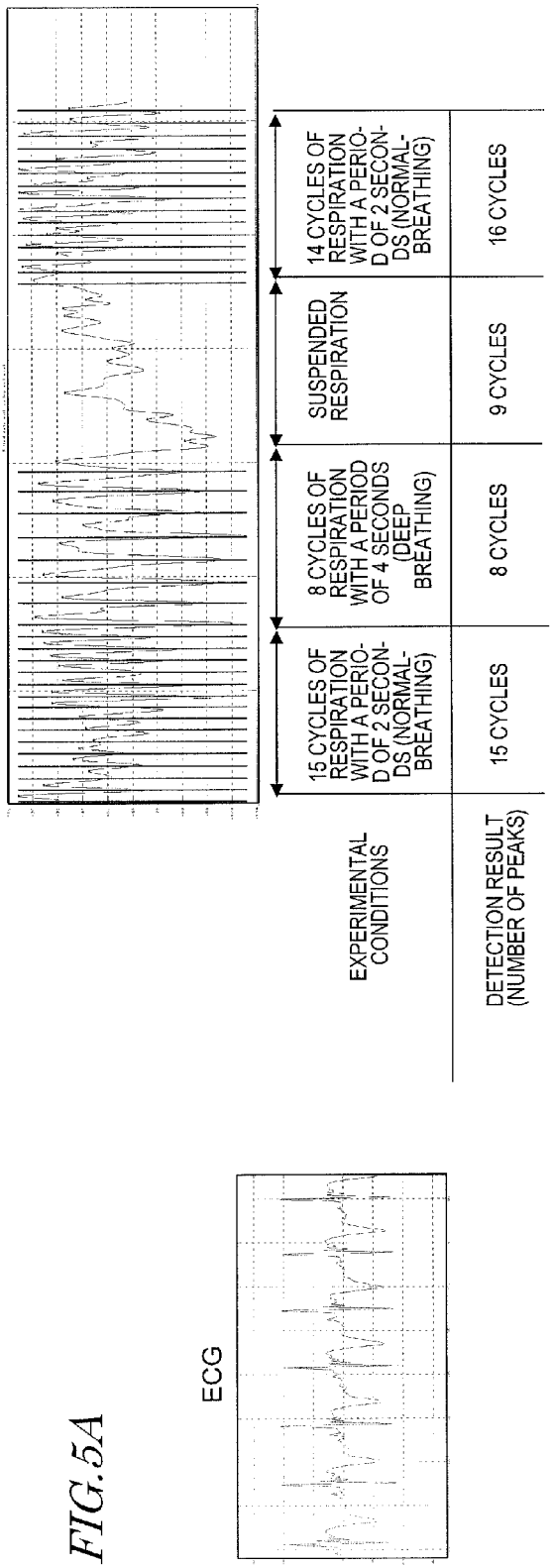
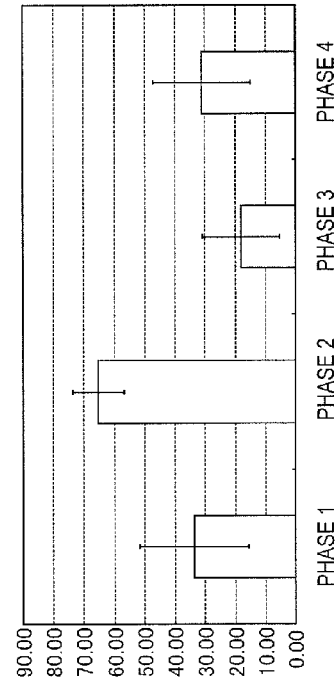

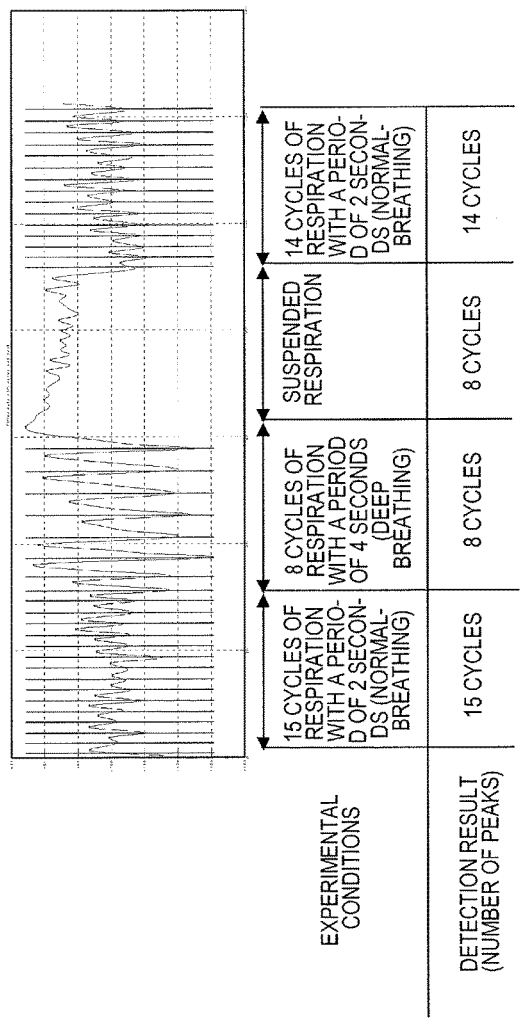
FIG.17B
FIG.17A
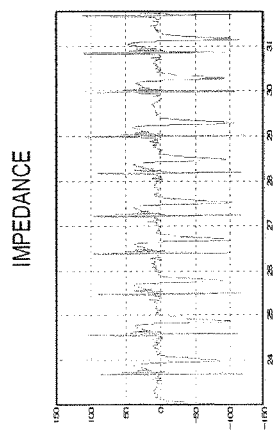
FIG.17D
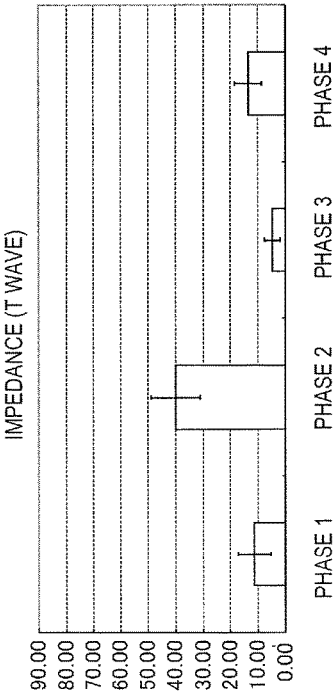
FIG.17C

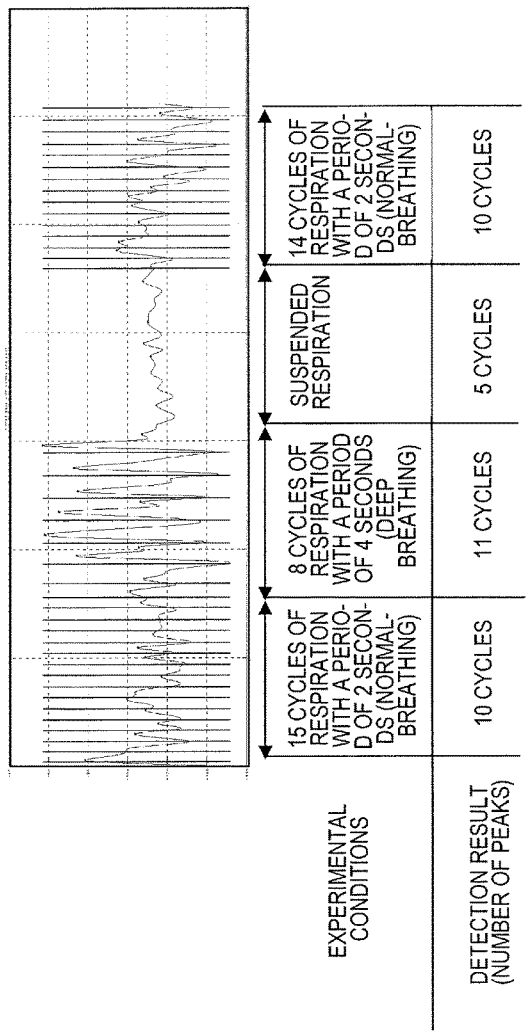
*FIG.18B*
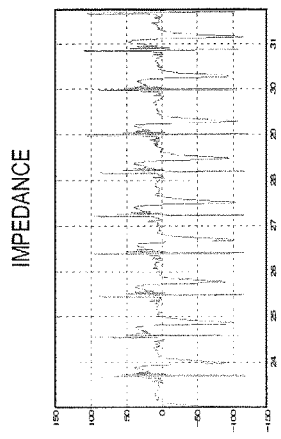
*FIG.18A*
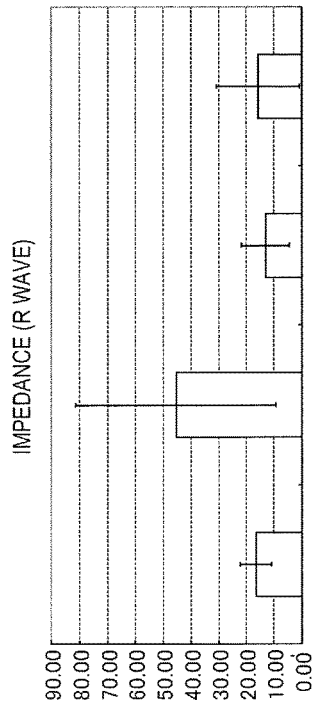
*FIG.18D*
*FIG.18C*

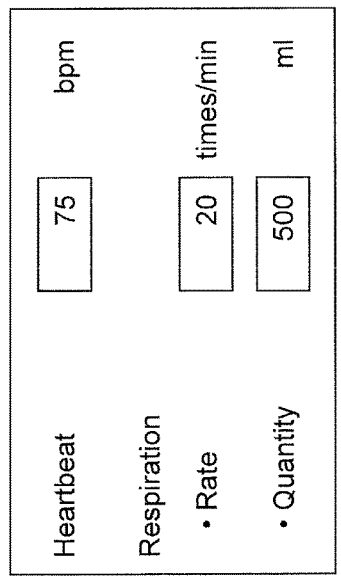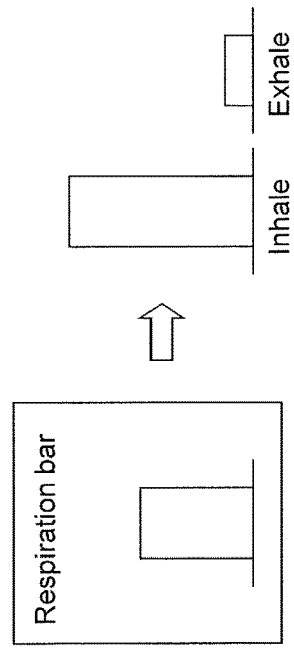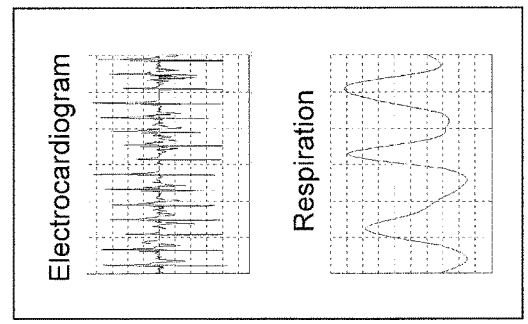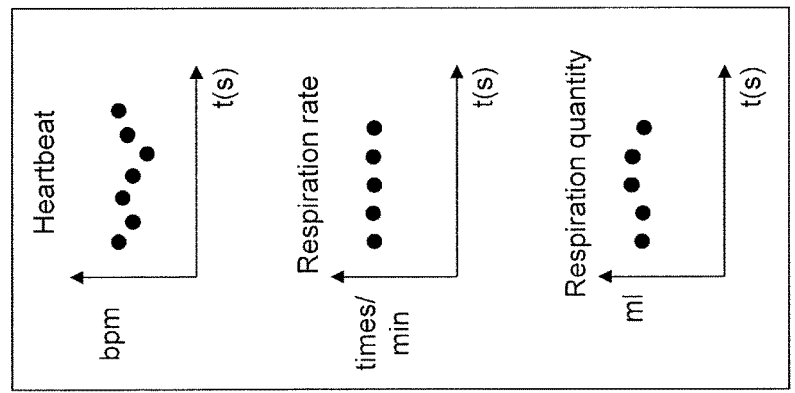

ENVELOPE

ENVELOPE

● DETECTED T WAVE PEAK

○ CALIBRATED T WAVE PEAK

BIOLOGICAL SIGNAL MEASUREMENT SYSTEM, APPARATUS, METHOD, AND COMPUTER PROGRAM THEREOF

This is a continuation of International Application No. PCT/JP2014/000587, with an international filing date of Feb. 4, 2014, which claims priority of Japanese Patent Application No. 2013-060214, filed on Mar. 22, 2013, the contents of which are hereby incorporated by reference.

BACKGROUND

1. Technical Field:

The present application relates to a technique of extracting respiration. More specifically, the present application relates to a technique of extracting information concerning respiration, by measuring biological impedance with a plurality of electrodes which are worn on the body of a user.

2. Description of the Related Art:

In recent years, methods of electrically and mechanically measuring and recording the physical status of a user over long hours are becoming increasingly popular. Examples of basic electrical information representing the physical status of a user include the electroencephalogram (EEG), which is related to the brain, and the electrocardiogram (ECG), which is related to motions of the heart. Between these, an electrocardiogram may be acquired at a hospital as fundamental biological information (vital signs), for example. An electrocardiogram may also be acquired when a heart disease is suspected, by using a portable-type electrocardiograph called the Holter electrocardiograph. Use of the Holter electrocardiograph makes it possible to record an electrocardiogram at places other than a hospital, such as one's own home, over long hours, e.g., 24 hours. In recent years, the Holter electrocardiograph has been downsized, making it easier for a user to measure electrocardiograms.

Recording an electrocardiogram over long hours with a Holter electrocardiograph makes it possible to discover symptoms such as arrhythmia, which cannot be detected through short-time checkups at hospital. However, apart from the electrocardiogram, there are checkup items (clinical cases) which can only be exposed through long hours of checkup, e.g., sleep apnea syndrome. Sleep apnea syndrome is a disease of the respiratory system that is deeply related to arrhythmia.

Assessments of sleep apnea syndrome cannot be made with electrocardiograms alone, but also require information concerning respiration. Currently, a sleep apnea syndrome assessment requires an overnight polysomnography checkup, which simultaneously takes electrocardiogram, respiration, and electroencephalogram measurements. This checkup needs to be conducted during an overnight stay at hospital, which presents significant burdens on the hospital and on the patient. Therefore, mere suspicion of a disease possibility would not practically justify such a high-burden checkup.

If it were possible to obtain information concerning diseases of the respiratory system—or specifically, respiratory rate-related information—, as easily as if obtaining an electrocardiogram with a Holter electrocardiograph, it would further promote early disease detection and quickened diagnosis.

When measuring respiration in simple manners, the main choice so far has been a medical device called the pulse oximeter. This is a measuring device for examining arterial oxygen saturation. Arterial oxygen saturation is measured with a sensor worn at the fingertip, called a probe. This measuring device, which includes a red light source (LED), measures the oxygen content in the arteries inside a finger in real time by measuring light transmitted through the finger with the sensor as red light is emitted from the LED. Thus, when both electrocardiogram and respiration information is necessary, it has been necessary to wear the electrodes for an electrocardiograph on the thorax, and wear the probe of a pulse oximeter at the fingertip.

What has been done so far is to use a single apparatus to simultaneously acquire electrocardiogram and respiration information, and isolate respiration information from the acquired data by using electrocardiogram information. One approach is the impedance method. Under the impedance method, an electric current is flown in the user's body, and impedance changes associated with the electrocardiogram and respiration are measured with electrodes which are placed on the thorax. For example, the specification of Japanese Patent No. 3735774 discloses a method for removing the respiratory component from thoracic impedance.

FIG. 1A shows fundamental components of an electrocardiogram. In FIG. 1A, the Q, R, and S waves represent ventricular excitation.

FIG. 1B shows an example waveform which is obtained as an electrocardiogram. In the specification of Japanese Patent No. 3735774, an electrocardiographic component is estimated based on a linear combination model of cosine components and sine wave components of harmonics whose fundamental wave is the R-R interval of an electrocardiogram. This method is called the SFLC (Scaled Fourier Linear Combiner) method.

Yoshifumi Yasuda, et. al., "Modified thoracic impedance plethysmograph to monitor sleep apnea syndromes", Sleep Medicine, Vol. 6, pp. 215-224 (2005) (hereinafter referred to as "Non-Patent Document 1") discloses a technique which, by utilizing the method described in the specification of Japanese Patent No. 3735774, obtains a respiratory component by subtracting an electrocardiographic component which is estimated by the SFLC method from thoracic impedance. FIG. 2 shows the concept behind the conventionally-employed technique of extracting a respiratory component (c) by subtracting a component of electrocardiographic origin (b) from thoracic impedance (a). If there is a change in respiration, it is reflected in the waveform of the extracted respiratory component.

FIGS. 3A and 3B show impedance changes when changes occur in respiration. FIG. 3A shows impedance changes in the case where normal respiration is followed by a state of low respiration, and further followed by normal respiration. It can be seen that the amplitude itself decreases in the zone of low respiration. FIG. 3B shows impedance changes in the case where a state of obstructive apnea is created after normal respiration. It can be seen in this case that, in the zone of apnea, the amplitude of impedance is lost altogether. Thus, impedance changes not only reflect the respiratory rate, but also reflect the aspiration volume.

Another approach is the ECG (Electrocardiogram) method. Under the ECG method, potential changes based on an electrocardiogram and respiration are measured with electrodes which are placed on the thorax, without flowing an electric current. Ciara O'Brien, Conor Heneghan, "A comparison of algorithms for estimation of a respiratory signal from the surface electrocardiogram", Computers in Biology and Medicine, Vol. 37, Issue 3, pp. 305-314 (2007) (herein referred to as "Non-Patent Document 2) discloses a technique of extracting a respiratory component by finding an envelope of R waves on the time axis.

SUMMARY

Various conditions exist when taking actual measurements of biological information, e.g., severity of the patient's symptoms, needed accuracy of biological information, and burden on the patient. Therefore, the more selectable measurement methods, the better. In other words, in the context of biological information measurements, there was a need for developing a novel measurement method.

One non-limiting, and exemplary embodiment of the present disclosure provides a technique for acquiring biological information concerning respiration.

In order to solve the aforementioned problems, one implementation of the present disclosure encompasses a biological information measurement system including: a plurality of electrodes; a current source connected to the plurality of electrodes to supply a current thereto; a measurement unit configured to measure impedance from a potential difference between the plurality of electrodes; a detector configured to detect values of specific peaks from chronological data of the impedance; an envelope generator configured to generate an envelope of the values of specific peaks; and an output unit configured to output information of the envelope as biological information, such that, when the plurality of electrodes are provided on a thorax of a user, the detector detects T wave peak values of a component of electrocardiographic origin from the chronological data of the impedance, and the output unit outputs information of the envelope as biological information concerning a respiratory component of the user.

The aforementioned general or specific implementation can be implemented by using a system, a method, or a computer program, or alternatively by a combination of a system, a method, and a computer program.

With a biological signal measurement system according to one implementation of the present disclosure, a respiratory component can be extracted from thoracic impedance, whereby an electrocardiogram and a respiratory component can be measured in a simple manner. Moreover, a respiratory rate and a respiratory volume of the user can be estimated from the measured respiratory component, and presented to the user.

According to the above aspect, thoracic impedance is measured with a low current on the order of several nA, and a respiratory component is extracted therefrom. This results in reduced current consumption, and a battery-driven mobile device can be operated for long hours to obtain biological information.

BRIEF DESCRIPTION OF THE DRAWINGS

FIGS. 5A to 5D are diagrams showing results of applying the method of Non-Patent Document 2 to a measured ECG.

FIGS. 17A to 17D are diagrams showing results of ascertaining a respiratory component by utilizing an envelope of T waves, with respect to thoracic impedance which is measured with a sine wave current of ±10 nA.

FIGS. 18A to 18D are diagrams showing results of ascertaining a respiratory component by utilizing an envelope of R waves, with respect to thoracic impedance which is measured with a current of 10 nA.

FIGS. 19A to 19D are diagrams showing example displays made by a respiratory output unit 9 on a screen.

DETAILED DESCRIPTION

The inventors have studied problems associated with the traditional method of isolating respiration information from electrocardiogram information.

In the method of Non-Patent Document 1, a current of several hundred microamperes (μA), e.g., a 350 μA current, is flown in order to measure thoracic impedance. When power is always stably available, there is no problem in continuously flowing a current of this level. On the other hand, when a current of this level is flown in a mobile-type measuring instrument which is battery-driven, battery capacity issues will not permit sufficient life. In order to guarantee a battery life, impedance measurements need to be taken with a lower current (e.g., a current of several nano-amperes (nA)).

Figure 4A:
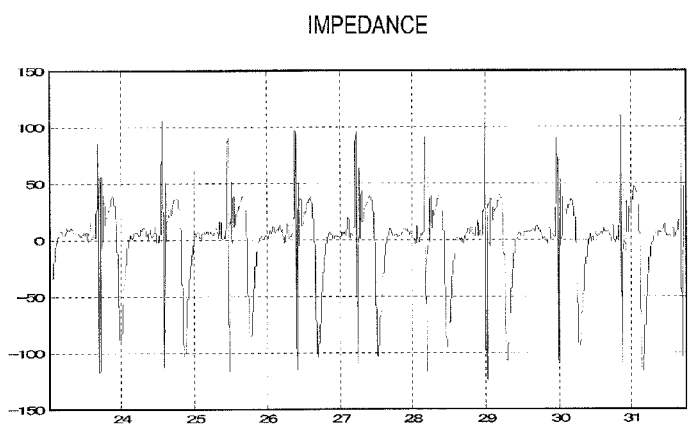
FIGS. 4A and 4B are diagrams showing results of applying the method of Non-Patent Document 1 to thoracic impedance which is measured with a current of 10 nA.
Figure 4B:
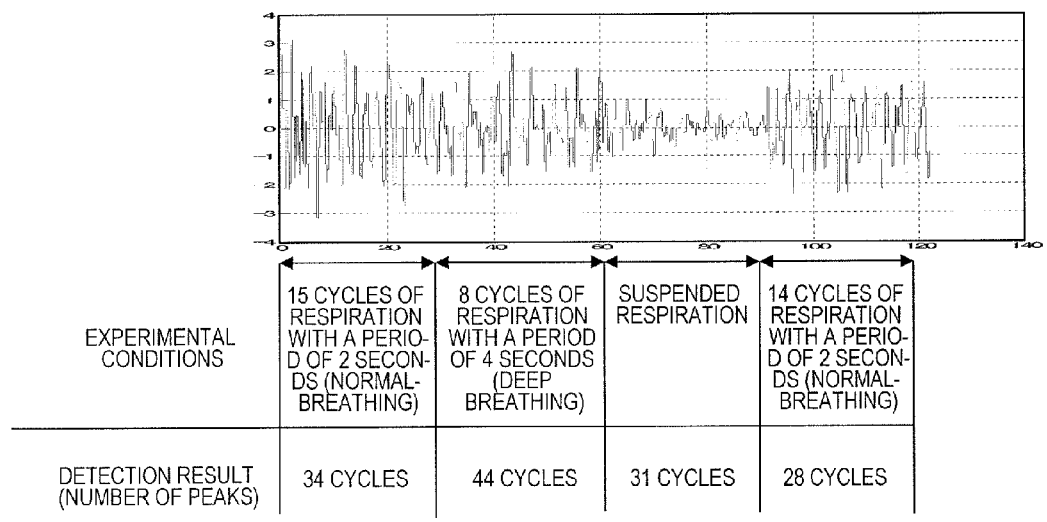

FIGS. 4A and 4B show results of applying the method of Non-Patent Document 1 to thoracic impedance which is measured with a current of 10 nA. FIG. 4A shows measured thoracic impedance, and FIG. 4B shows an extracted respiratory component. During measurement, the test subject was asked to consecutively undergo four manners of respiration:
Phase 1: 15 cycles of respiration with a period of 2 seconds (normal breathing)
Phase 2: 8 cycles of respiration with a period of 4 seconds (deep breathing)
Phase 3: suspended respiration
Phase 4: 14 cycles of respiration with a period of 2 seconds (normal breathing).

From the extracted respiratory component, the same number of peaks as the actual respiratory rate must be detected. However, as will be understood from FIG. 4B, the detected number of peaks was different from the actual respiratory rate which was provided as an experimental condition.

Figure 2:
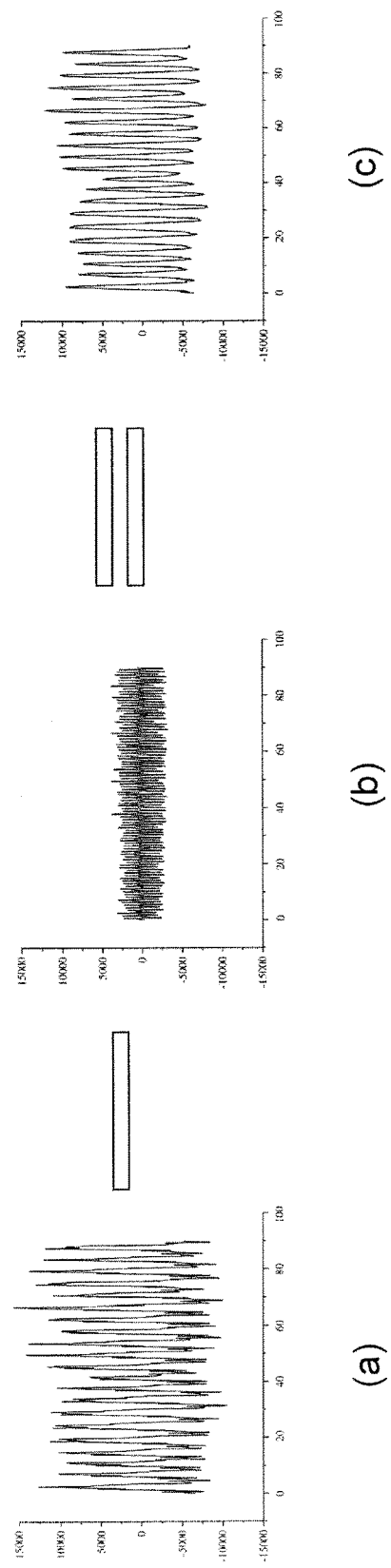
FIG. 2 is a diagram illustrating the concept behind a conventionally-employed technique of extracting a respiratory component from thoracic impedance.
Figure 3A:
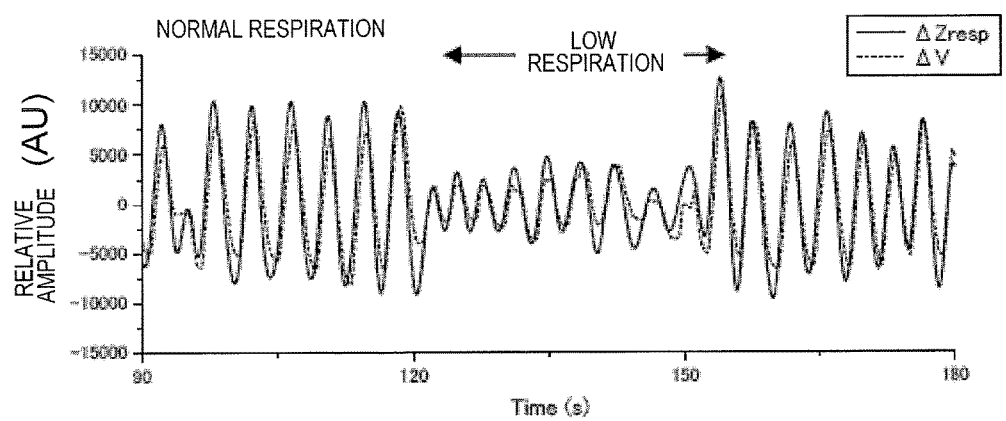
FIGS. 3A and 3B are diagrams showing impedance changes when changes occur in respiration.
Figure 3B:
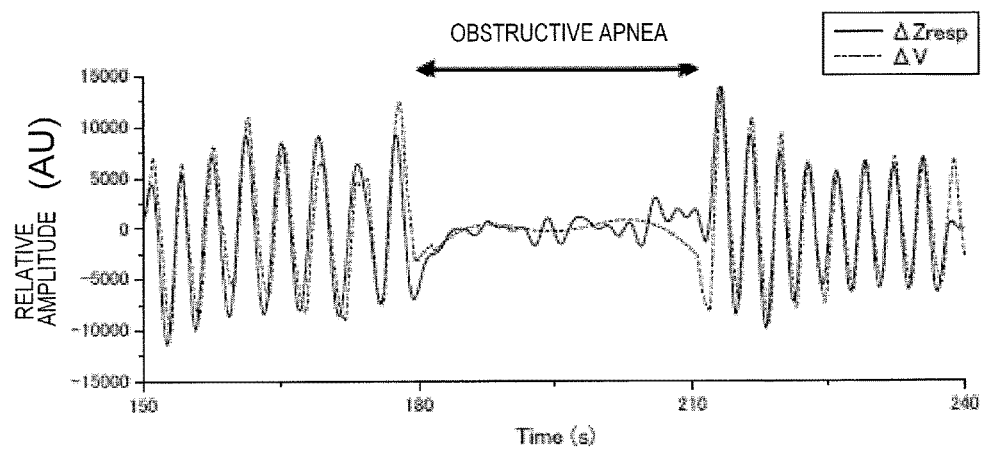

In searching for reasons why the respiratory component cannot be correctly extracted, the inventors have paid attention to the relative magnitudes of the electrocardiographic component and the respiratory component. As shown in FIG. 2, when thoracic impedance (a) was measured with a current of several hundred μA (350 μA), a respiratory component (c) which was greater than the electrocardiographic component (b) was obtained. However, as shown in FIG. 4A, taking measurements with a current of several nA (10 nA) results in an electrocardiographic component which is greater than the respiratory component. In this case, even if an electrocardiographic component which is estimated by the SFLC method is subtracted from the thoracic impedance, some periodicity of the electrocardiogram will be left, making it impossible to correctly extract the respiratory component.

FIGS. 5A to 5D show results of applying the method of Non-Patent Document 2 to a measured ECG. FIG. 5A shows a measured ECG, FIG. 5B shows an extracted respiratory component. FIG. 5C is a bar chart showing an arithmetic mean and a standard deviation of amplitude in each phase. FIG. 5D shows values of arithmetic mean and standard deviation of amplitude in each phase.

In Phase 1 and Phase 2, the same number of peaks as the actual respiratory rate was detected. In Phase 3 and Phase 4, however, the detected number of peaks was different from the actual respiratory rate. As shown in FIGS. 5C and 5D, an arithmetic mean amplitude in each phase is correlated with the actual respiratory volume. However, because of the large standard deviation, it is difficult to estimate the respiratory volume on the basis of amplitude.

Accordingly, the inventors have studied a method of isolating respiration information from electrocardiogram information, and consequently developed a technique which enables it. As will be described in detail below, by correctly isolating respiration information from electrocardiogram information, it becomes possible to simultaneously measure an electrocardiogram and respiration (respiratory rate, respiratory volume) by using the same electrodes. With this technique, respiration information can be correctly isolated from electrocardiogram information even by flowing a low current on the order of several nA. Therefore, the technique makes it possible to keep acquiring biological information for long hours by using a mobile device which is battery-driven and has limited power availability.

Hereinafter, the findings obtained by the inventors will be described, followed by a description of each embodiment of the biological signal measurement system according to the present disclosure.

(Findings Forming the Basis of the Present Disclosure)

The inventors have found that the traditional method of isolating respiration information from electrocardiogram information has the following problems.

In the method of Non-Patent Document 1, a current of several hundred μA (350 μA) is flown in order to measure thoracic impedance. On the other hand, in a mobile-type measuring instrument, flowing a current of several hundred μA will not permit sufficient battery life. This makes it necessary to measure impedance with a low current (e.g., a current of several nA).

To say that a respiratory component has been accurately detected requires that the number of peaks in the respiratory component as extracted from a thoracic impedance (FIG. 4A) which is measured with a low current equals the actual respiratory rate. However, as shown in FIG. 4B, the number of peaks in the respiratory component would differ from the actual respiratory rate.

The inventors have found that the reason for inability to correctly extract the respiratory component lies in the relative magnitudes of the electrocardiographic component and the respiratory component.

Possible reasons thereof may be that, as discussed above: taking measurements with a current of several nA (10 nA) results in an electrocardiographic component which is greater than the respiratory component as shown in FIG. 4A; and in that case, even if an electrocardiographic component which is estimated by the SFLC method is subtracted from the thoracic impedance, some periodicity of the electrocardiogram will be left, making it impossible to correctly extract the respiratory component.

Figure 1A:
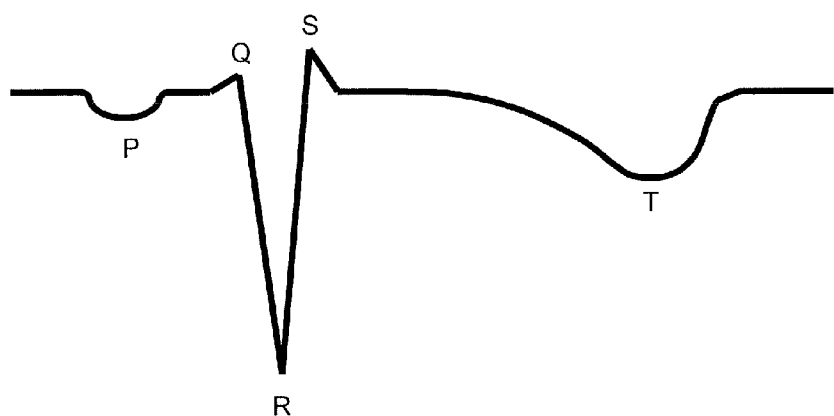
FIG. 1A is a diagram showing fundamental components of an electrocardiogram.

It also turned out that, as shown in FIGS. 5C and 5D, although an arithmetic mean amplitude in each phase is correlated with the actual respiratory volume, the large standard deviation for amplitude makes it difficult to estimate the respiratory volume on the basis of amplitude. Thus, the inventors have arrived at the conclusion that respiratory volume needs to be estimated from information other than amplitude. Then, as will be described later, the inventors have found that respiration information can be correctly isolated from electrocardiogram information by utilizing T waves as shown in FIG. 1A.

This technique makes it possible to simultaneously measure an electrocardiogram and respiration (respiratory rate, respiratory volume) by using the same electrodes. Moreover, even when thoracic impedance is measured with a low current on the order of several nA (10 nA), respiration information can be correctly isolated from electrocardiogram information. Therefore, the technique makes it possible to keep acquiring biological information for long hours by using a mobile device which is battery-driven and has limited power availability.

(Thoracic Impedance Measurement)

As methods of measuring impedance of the thorax, the two-terminal method and the four-terminal method are known.

In the two-terminal method, two electrodes are employed to adhere to the skin. While flowing a current through via the two electrodes, a potential difference is measured. In other words, in the two-terminal method, the electrodes for flowing the current and the electrodes for taking impedance measurements are identical.

In the four-terminal method, four electrodes are employed to adhere to the skin. A current is flown via two electrodes, while a potential difference between two points in the current path within the body is measured by using the other two electrodes. In other words, in the four-terminal method, the electrodes for flowing the current are distinct from the electrodes for taking impedance measurements. As the measurement conditions for the four-terminal method, it is necessary that the two electrodes for measuring a potential difference be located within the path of the current flowing in the body.

Figure 6A:
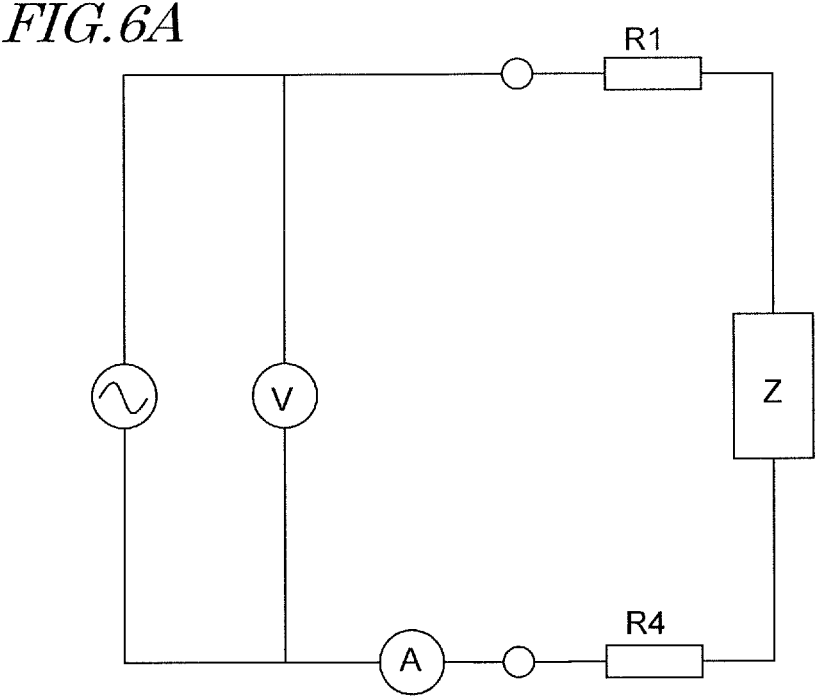
FIG. 6A is a diagram showing a schematic circuit construction under the two-terminal method.
Figure 6B:
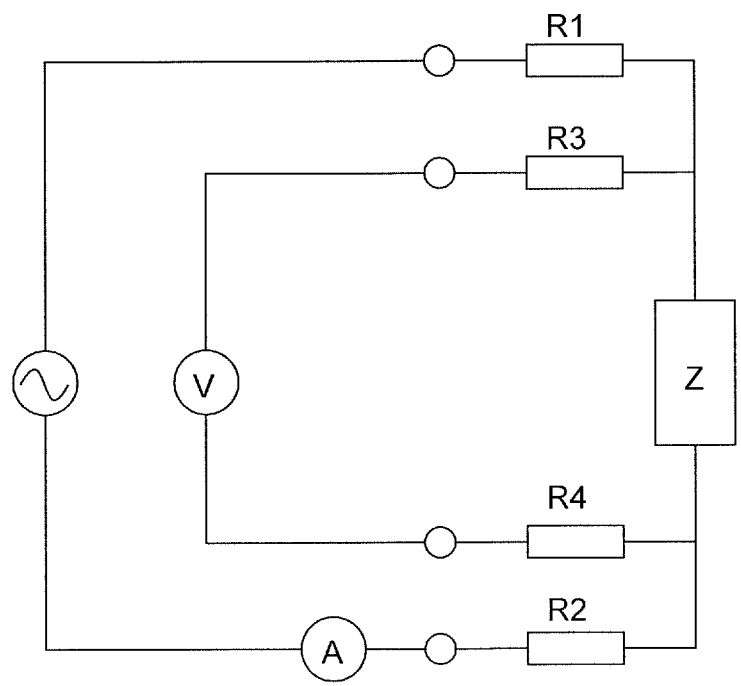
FIG. 6B is a diagram showing a schematic circuit construction under the four-terminal method.

FIG. 6A shows a schematic circuit construction under the two-terminal method, and FIG. 6B shows a schematic circuit construction under the four-terminal method. denotes impedance of a target of measurement, and R1 to R4 denote contact impedances between the respective electrodes and the skin. In the figures, each "○" corresponds to an electrode.

In the two-terminal method of FIG. 6A, Z+R1+R2 is measured. In the four-terminal method of FIG. 6B, Z alone is measured. Therefore, the four-terminal method is chosen when it is desirable to eliminate the influence of contact impedance between electrodes and the skin when measuring thoracic impedance. In other words, an impedance which is measured by the four-terminal method has a higher accuracy than does an impedance which is measured by the two-terminal method.

Changes in thoracic impedance are based on the heart activity (heartbeats) and the lung activity (respiration). The reason why impedance changes occur due to heart activity (heartbeats) is that the cardiac muscle cells are electrically excited (depolarized) and return to normal (repolarize) as the heart undergoes the mechanical activities of contraction and expansion. The electrical changes in the cardiac muscle cells cause changes in impedance. On the other hand, the reason why impedance changes occur due to lung activity (respiration) is as follows. When inhaling, air is taken into the alveoli, thus making it difficult for an electric current to flow; this results in a high impedance. When exhaling, air is discharged, thus making it easier for an electric current to flow; this results in a low impedance. When impedance is measured with electrodes adhering to both hands, the impedance between both hands manifests changes due to heartbeats and changes due to respiration.

The inventors have arrived at a technique of detecting T wave peak values of a component of electrocardiographic origin from chronological data of thoracic impedance, and correctly isolating respiration information therefrom.

In summary, one implementation of the present disclosure is as follows.

A biological information measurement system as one implementation of the present disclosure comprises: a plurality of electrodes; a current source connected to the plurality of electrodes to supply a current thereto; a measurement unit configured to measure impedance from a potential difference between the plurality of electrodes; a detector configured to detect values of specific peaks from chronological data of the impedance; an envelope generator configured to generate an envelope of the values of specific peaks; and an output unit configured to output information of the envelope as biological information.

In one embodiment, the plurality of electrodes are provided on a thorax of a user; and, as the values of the specific peaks, the detector detects T wave peak values of a component of electrocardiographic origin from chronological data of the impedance, and the output unit outputs information of the envelope as biological information concerning a respiratory component of the user.

In one embodiment, the impedance measured by the measurement unit contains a component of electrocardiographic origin and a component of respiratory origin; and in the impedance, the component of electrocardiographic origin is greater than the component of respiratory origin.

In one embodiment, the current source supplies a current of not less than 1 nA and not more than 107.62 µA.

In one embodiment, the current source supplies a current smaller than 350 µA.

In one embodiment, the detector detects each T wave peak value by using a value of a peak in chronological data of the impedance, and a period of time from a point in time of reaching the peak until a point in time of returning to a predetermined baseline.

In one embodiment, the detector detects R wave peaks of a component of electrocardiographic origin, and determines a peak of largest amplitude that is contained between adjacent R wave peaks as a T wave peak.

In one embodiment, the envelope generator interpolates between detected T wave peaks with a spline curve to generate an envelope.

In one embodiment, the biological information measurement system further comprises a respiratory rate estimation unit configured to estimate a respiratory rate from information of the respiratory component output by the output unit.

In one embodiment, the respiratory rate estimation unit calculates a last period of the respiratory component by using local maximums or local minimums during estimation, and estimates the respiratory rate by using the last period.

In one embodiment, the respiratory rate estimation unit estimates a respiratory rate at every fixed time interval.

In one embodiment, when a last amplitude of the respiratory component is equal to or less than a specific threshold value, the respiratory rate estimation unit detects suspended respiration and estimates the respiratory rate to be zero.

In one embodiment, the biological information measurement system further comprises a respiratory volume estimation unit configured to estimate a respiratory volume from information of the respiratory component output by the output unit.

In one embodiment, the respiratory volume estimation unit estimates a respiratory volume at every fixed time interval.

In one embodiment, the respiratory volume estimation unit estimates the respiratory volume per cycle based on the level of a last amplitude of the respiratory component.

In one embodiment, the respiratory volume estimation unit detects suspended respiration when a last amplitude of the respiratory component is equal to or less than a specific threshold value during estimation, and estimates the respiratory volume to be zero.

In one embodiment, the biological information measurement system further comprises a calibrator configured to, when a value of a specific peak of an electrocardiographic component detected by the detector is smaller than a predetermined threshold value, calibrate the value of the specific peak.

In one embodiment, the calibrator determines a last period in the respiratory component from specific peaks at previous points in time, and, as a calibration value, inputs a value of a specific peak that stands closest to a point in time obtained by subtracting the last period from a point in time of the specific peak which is smaller than the predetermined threshold value, into the value of the specific peak which is smaller than the predetermined threshold value.

A biological information computation apparatus as another implementation of the present disclosure comprises: a detector configured to receive chronological data of impedance which is measured from a potential difference between a plurality of electrodes provided on a thorax of a user by using a current supplied from a current source, and detect T wave peak values of a component of electrocardiographic origin from the chronological data; an envelope generator configured to generate an envelope of the T wave peak values; and an output unit configured to output information of the envelope as biological information concerning a respiratory component of the user.

In one embodiment, the plurality of electrodes are provided on a thorax of a user; and, as the values of the specific peaks, the detector detects T wave peak values of a component of electrocardiographic origin from chronological data of the impedance, and the output unit outputs information of the envelope as biological information concerning a respiratory component of the user.

A biological information measurement method as still another implementation of the present disclosure comprises the steps of: supplying a current to a plurality of electrodes provided on a thorax of a user; measuring impedance from a potential difference between the plurality of electrodes; from chronological data of the impedance, detecting T wave peak values of a component of electrocardiographic origin; generating an envelope of the T wave peak values; and outputting information of the envelope as biological information concerning a respiratory component of the user.

In one embodiment, the plurality of electrodes are provided on a thorax of a user; and the detecting step detects T wave peak values of a component of electrocardiographic origin from chronological data of the impedance, and the outputting step outputs information of the envelope as biological information concerning a respiratory component of the user.

A computer program to be executed by a computer provided in a biological information measurement system as still another implementation of the present disclosure causes the computer to execute the steps of: receiving chronological data of impedance which is measured from a potential difference between a plurality of electrodes provided on a thorax of a user by using a current supplied from a current source; detecting T wave peak values of a component of electrocardiographic origin from the chronological data; generating an envelope of the T wave peak values; and outputting information of the envelope as biological information concerning a respiratory component of the user.

In one embodiment, the plurality of electrodes are provided on a thorax of a user; and the computer program causes the computer to: at the detecting step, detect T wave peak values of a component of electrocardiographic origin from chronological data of the impedance; and at the outputting step, output information of the envelope as biological information concerning a respiratory component of the user.

Hereinafter, with reference to the attached drawings, embodiments of the present disclosure will be described.

(Embodiment 1)

Figure 7:
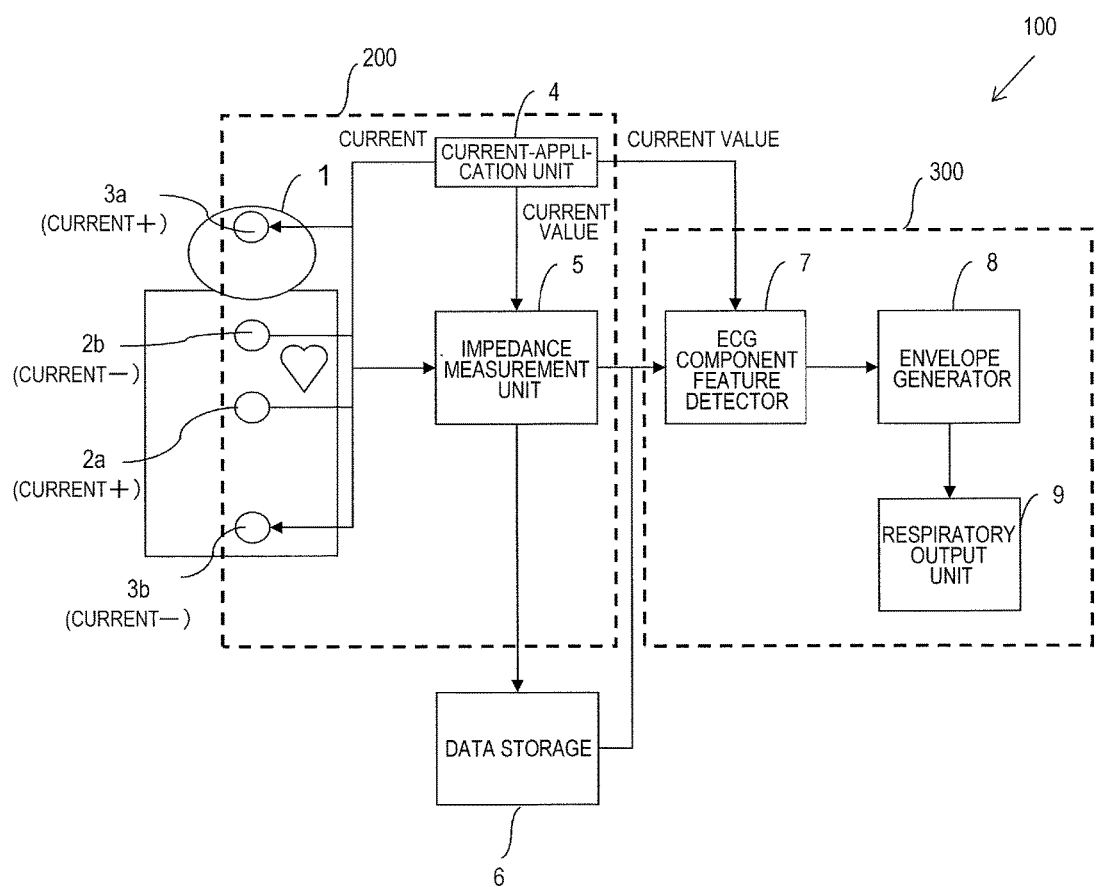
FIG. 7 is a diagram showing the construction of a biological information measurement system 100 according to Embodiment 1.

FIG. 7 shows the construction of a biological information measurement system 100 according to the present embodiment. The biological information measurement system 100 includes a data storage 6, a biological signal measurement apparatus 200, and a biological information computation apparatus 300.

The biological signal measurement apparatus 200 at least includes potential-measurement electrodes 2a and 2b, current-application electrodes 3a and 3b, a current-application unit 4, and an impedance measurement unit 5.

The biological information computation apparatus 300 includes an ECG component feature detector 7, an envelope generator 8, and a respiratory output unit 9. The biological information computation apparatus 300 is connected in a wired or wireless manner to the biological signal measurement apparatus 200 and the data storage 6 so as to exchange information therewith.

Hereinafter, the construction of the biological signal measurement apparatus 200 and the biological information computation apparatus 300 will be described.

(Implementation of the Biological Signal Measurement Apparatus 200)

Figure 8C:
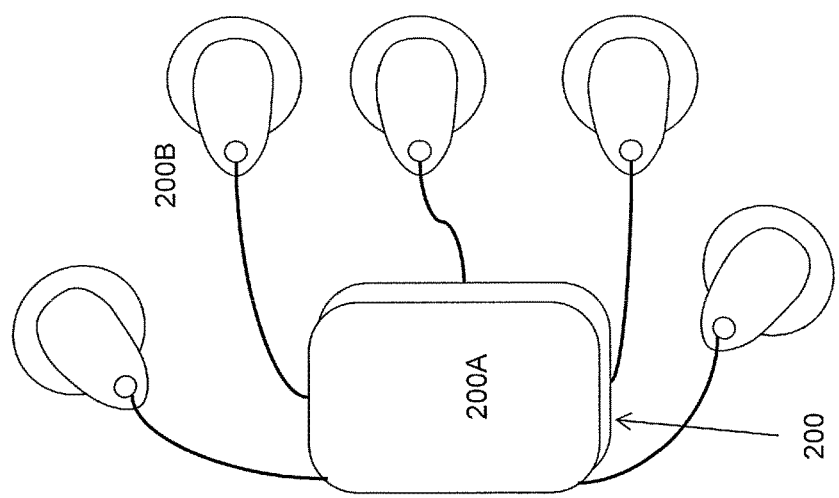
FIGS. 8A to 8C are exemplary implementations of a biological signal measurement apparatus 200 according to the present embodiment.
Figure 8B:
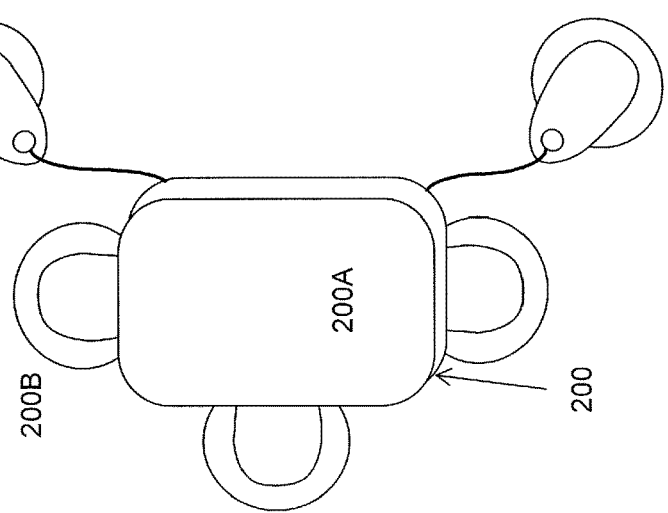
Figure 8A:
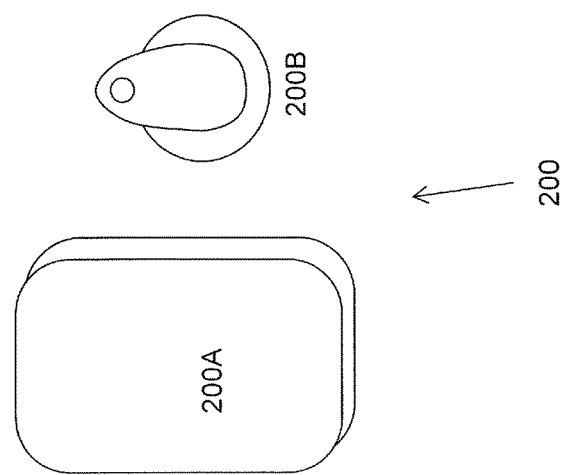

FIGS. 8A to 8C show exemplary implementations of the biological signal measurement apparatus 200 according to the present embodiment. The biological signal measurement apparatus 200 shown in FIG. 8A includes a measurement unit 200A and an electrode portion(s) 200B which are discrete from each other. The measurement unit 200A at least includes the current-application unit 4 and the impedance measurement unit 5. The electrode portion(s) 200B corresponds to the potential-measurement electrodes 2a and 2b and the current-application electrodes 3a and 3b.

As many electrode portions 200B as are necessary for measurement are provided. For example, in order to measure a potential between two points, two electrodes may be used, or the following three may be used: a measurement electrode, ground, and a reference electrode.

In order to supply a current, two more electrodes are used. They may be of any material having a high electrical conductivity; metal electrodes for medical use, disposable electrodes, or the like can be used. The electrode portion(s)

200B is provided in direct contact with the thorax of the user (test subject), so as to enable biological potential measurement. The electrode portion(s) 200B and the measurement unit 200A are to be connected in a manner of reducing electrical resistance.

For example, FIG. 8B shows an example of constructing the electrode portions 200B from disposable electrodes for medical use. In the case of snap-type electrodes, the electrode portions 200B are to be directly connected to the measurement unit 200A via snaps. A disposable electrode includes an adhesive portion which is made of a tackiness agent and an electrode portion. A disposable electrode is to be fixed on the user's body based on the adhesion of the adhesive portion.

FIG. 8C shows another example of constructing the electrode portion 200 from disposable electrodes for medical use. The example illustrates a case where the electrode portions 200B are connected to measurement unit 200A via cables. This example is suitable in the case where some distance is needed between electrodes, or where some distance is needed between the measurement unit 200A and the electrode portions 200B, for example. The electrode portions 200B are connected to the measurement unit 200A via the cables for supplying a current.

In any of FIGS. 8A to 8C above, the biological signal measurement apparatus 200 can be realized in a size that can fit on a palm, for example.

Next, the component elements of the biological signal measurement apparatus 200 and the biological information computation apparatus 300 will be described in detail. Although the following description mainly concerns functions, hardware construction of the biological signal measurement system 100 will be later be described in detail with reference to FIG. 36.

(Potential-measurement Electrodes 2a and 2b, Current-application Electrodes 3a and 3b)

FIG. 7 will be referred to again.

The potential-measurement electrodes 2a and 2b and the current-application electrodes 3a and 3b are allowed to adhere to the body surface of the user. The potential-measurement electrodes 2a and 2b are electrically connected to the impedance measurement unit 5, described later, to constitute an electric circuit. The potential-measurement electrodes 2a and 2b are electrically connected to the current-application unit 4, described later, to constitute an electric circuit.

(Electrode Positions)

Figure 9:
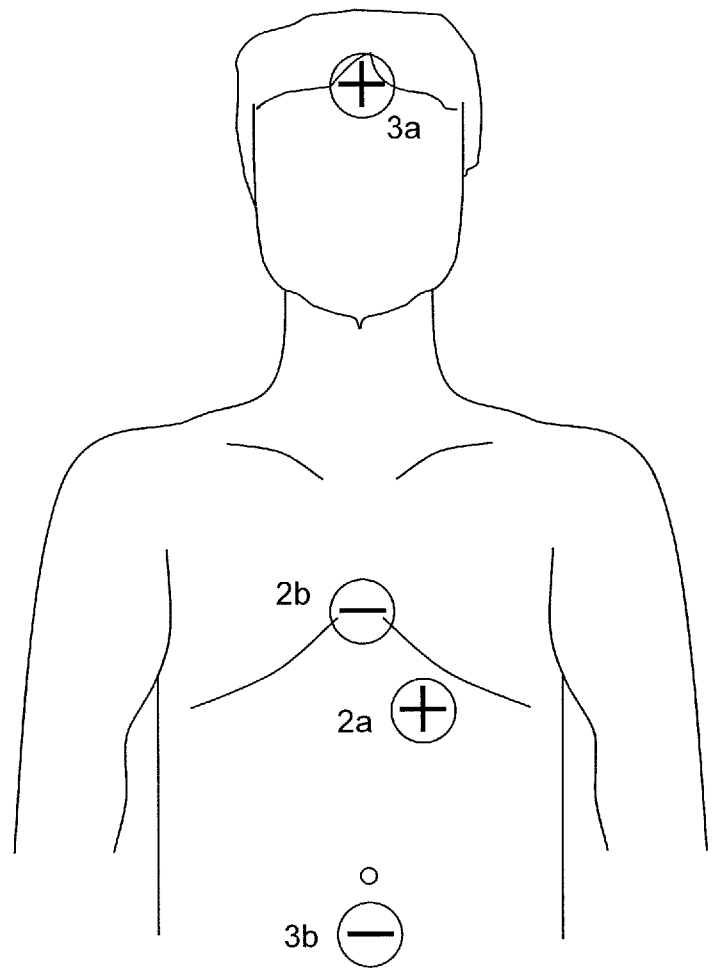
FIG. 9 is a diagram showing the relationship between the thorax of a user, potential-measurement electrodes 2a and 2b and current-application electrodes 3a and 3b, and positions of attachment on the thorax.
Figure 10:
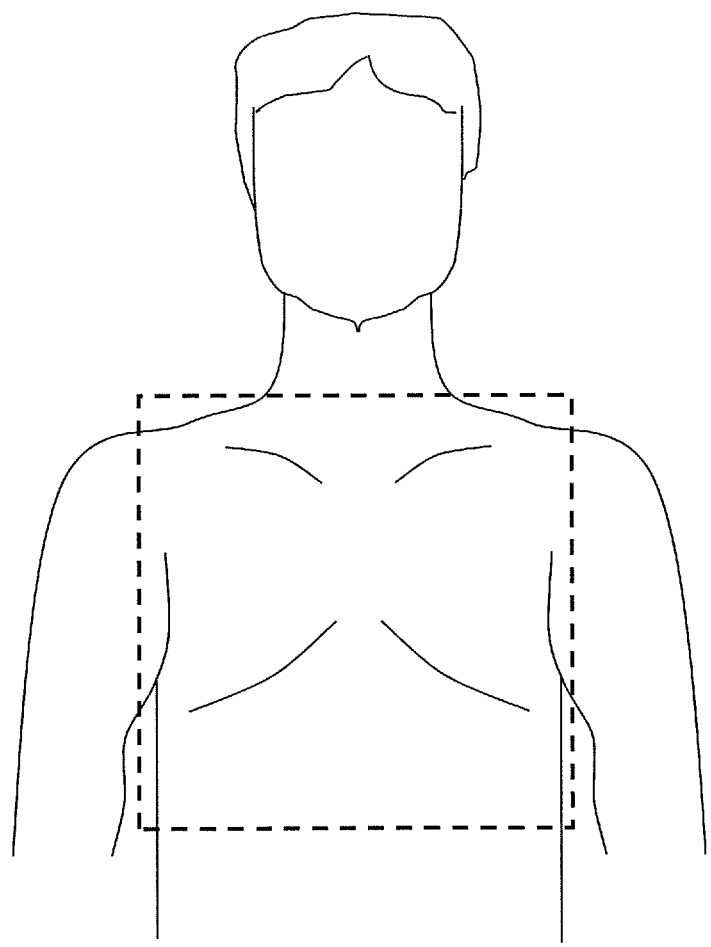
FIG. 10 is diagram showing the thorax of a user.

FIG. 9 shows relative positioning of the thorax of a user, the potential-measurement electrodes 2a and 2b, the current-application electrodes 3a and 3b, and positions of attachment on the thorax. The potential-measurement electrodes 2a and 2b are placed on the thorax of the user. FIG. 10 shows the thorax of the user with a broken line.

In the present embodiment, an electrocardiogram of the user is measured by the four-terminal method. The current-application electrodes 3a and 3b and the potential-measurement electrodes 2a and 2b are placed in positions satisfying the measurement conditions for the four-terminal method. Specifically, the potential-measurement electrodes 2a and 2b are placed in a range where a current flowing from the current-application electrode 3a to the current-application electrode 3b will pass, for example.

Figure 1B:
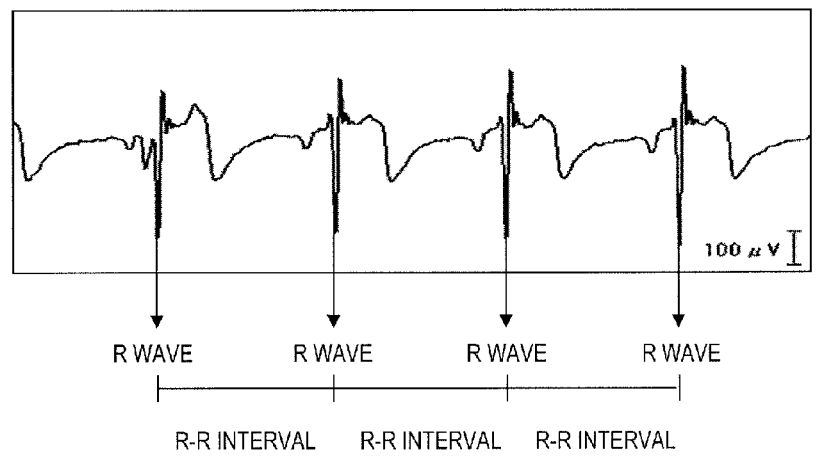
FIG. 1B is a diagram showing an example waveform which is obtained as an electrocardiogram.

In the present embodiment, following the description in Non-Patent Document 1, the positive (+) current-application electrode 3a is placed on the forehead, and the negative (−) current-application electrode 3b below the navel. Moreover, the positive and negative potential-measurement electrodes 2 are placed on the thorax, near the heart. In terms of the construction of the biological signal measurement apparatus 200 shown in FIG. 1B, for example, the negative (−) potential-measurement electrode 2b is placed at the inferior extremity of the sternum, and the positive (+) potential-measurement electrode 2a is placed on the left abdomen near the thorax.

Note that an electrocardiogram of the user can also be measured by the two-terminal method. When adopting the two-terminal method, the positive (+) potential-measurement electrode 2a and the negative (−) potential-measurement electrode 2b are to be employed. As shown in FIG. 9, the negative (−) potential-measurement electrode 2b may be placed at the inferior extremity of the sternum, and the positive (+) potential-measurement electrode 2a may be placed on the left abdomen near the thorax.

(Current-application Unit 4)

FIG. 7 will be referred to again.

The current-application unit 4, which is a so-called current source, supplies a current to the first current-application electrode 3a and the second current-application electrode 3b placed on the thorax of the user. In the present specification, supplying a current may also be expressed as applying a current. The current-application unit 4 is an internalized battery (not shown) and a circuit which is provided for allowing an electric current to flow from such a battery. Note that the current-application unit may be constructed without including an internalized battery.

In the present embodiment, the current value which is applied by the current-application unit 4 has a smaller value (e.g., several nA to several hundred μA) than current values which have conventionally been applied (e.g., 350 μA). This is in adaptation to the reduced battery (not shown) capacity of the biological signal measurement apparatus 200 as may be necessitated by its downsizing or the like. By measuring impedance with a current value which is lower than current values which have conventionally been applied, it becomes possible to extend the battery run time of the biological signal measurement apparatus 200. As mentioned above, in the present embodiment, the current-application unit 4 applies a current of a value which is smaller than 350 μA. The advantages described later will be realized with any such current value. However, more preferably, the current value to be applied by the current-application unit 4 may be in the range from 1 nA to 107.62 μA.

In the present embodiment, the current-application unit 4 applies an alternating current of a sine wave, with a current value of ±10 nA.

(Impedance Measurement Unit 5)

The impedance measurement unit 5 utilizes a potential difference between the first potential-measurement electrode 2a and the second potential-measurement electrode 2b to measure a thoracic impedance value of the user, at a plurality of points in time. Specifically, the impedance measurement unit 5 measures a potential difference between the potential-measurement electrodes 2a and 2b. The impedance measurement unit 5 acquires as a thoracic impedance value a value which is obtained by dividing the measured potential difference value by the current value applied by the current-application unit 4.

(Data Storage 6)

The data storage 6 is a recording device having a storage medium and/or a storage medium, for example. Examples of the storage medium include a semiconductor storage medium, a magnetic storage medium, an optical storage medium, or the like. The data storage 6 accumulates chronological impedance data.

(ECG Component Feature Detector 7)

The ECG component feature detector 7 utilizes the impedance data to detect specific peaks contained in the electrocardiographic component. In the present embodiment, the "specific peaks" are so-called T wave peaks. The principle behind T wave peak detection will be described with reference to FIG. 13.

(Envelope Generator 8)

The envelope generator 8 receives a result of specific peak detection by the ECG component feature detector 7. Then, the envelope generator 8 generates an envelope interconnecting the specific peaks. More specifically, the envelope generator 8 interpolates between T wave peaks with a spline curve, thus generating an envelope.

(Respiratory Output Unit 9)

The respiratory output unit 9 outputs the envelope which has been generated by the envelope generator 8 as a respiratory component. The mode of output may be a visual output on a screen or the like, for example, or writing data onto a storage medium, such data specifying the respiratory component.

(Overall Flow of Processes)

Figure 11:
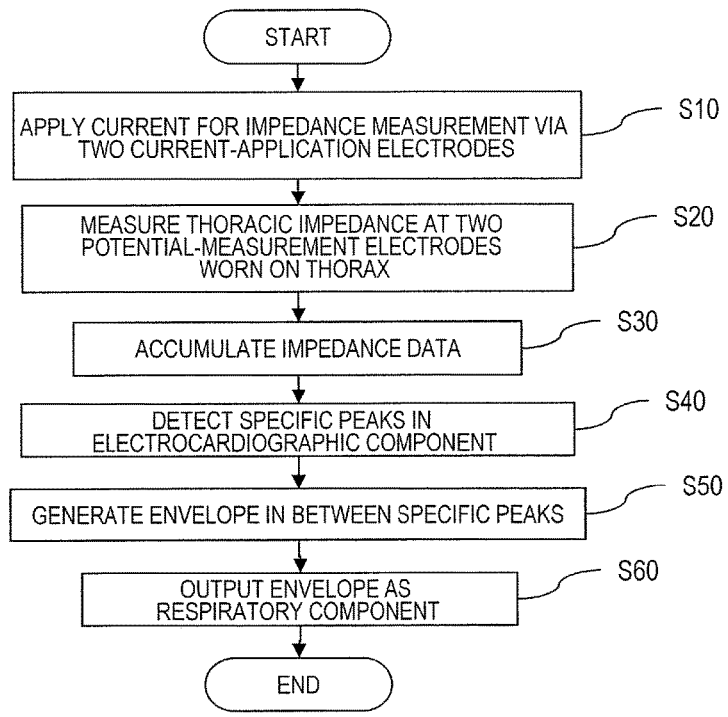
FIG. 11 is a flowchart showing an overall flow of processes by the biological information measurement system 100 according to an embodiment.

FIG. 11 shows an overall flow of processes by the biological information measurement system 100 according to the present embodiment.

<Step S10>

Via the current-application electrodes 3a and 3b worn on the user 1, the current-application unit 4 applies a current (10 nA) for impedance measurement.

Thoracic impedance includes the potential of a component of electrocardiographic origin and the potential of a component of respiratory origin. When the current value during measurement is sufficient large, e.g., 350 μA, the potential of the component of respiratory origin will be sufficiently greater than the potential of the component of electrocardiographic origin, thus allowing itself to be easily extracted.

On the other hand, in the present embodiment, the current value which is applied by the current-application unit 4 is much smaller than current values which have conventionally been applied (e.g., 350 μA). As a result of this, in the measured thoracic impedance, the component of electrocardiographic origin will be greater than the component of respiratory origin.

The current-application unit 4 sends information of the applied current value to the impedance measurement unit 5.

<Step S20>

The impedance measurement unit 5 measures thoracic impedance by utilizing a potential difference between the potential-measurement electrodes 2a and 2b worn on the thorax of the user 1. The impedance measurement unit 5 derives a thoracic impedance by dividing the potential difference which is measured between the potential-measurement electrodes 2a and 2b by the current value which is applied by the current-application unit 4. The potential difference is sampled at 1024 Hz or 512 Hz, for example. Data at each sampling point is sent to the next step.

<Step S30>

The impedance measurement unit 5 accumulates the measured thoracic impedance in the data storage 6. In the present embodiment, in order to factor in the capacity of the internal memory (not shown) of the impedance measurement unit 5, only the impedance data that pertains to a predetermined period of time, e.g., past 10 seconds, is to be accumulated in the internal memory. The data format for accumulation may be: the point in time of measurement; and the measured potential difference or impedance value. The impedance measurement unit 5 sequentially accumulates data which has reached the predetermined period of time into the data storage 6.

<Step S40>

By utilizing the impedance data up to the present that has been accumulated at step S30 and the impedance data measured at step S20, the ECG component feature detector 7 detects specific peaks in the electrocardiographic component.

As shown in FIG. 1A, an electrocardiogram contains peaks of the P wave, the Q wave, the R wave, the S wave, and the T wave as the fundamental components. In the present disclosure, T wave peaks are utilized. The details of the method of T wave peak detection will be described later.

<Step S50>

Figure 12:
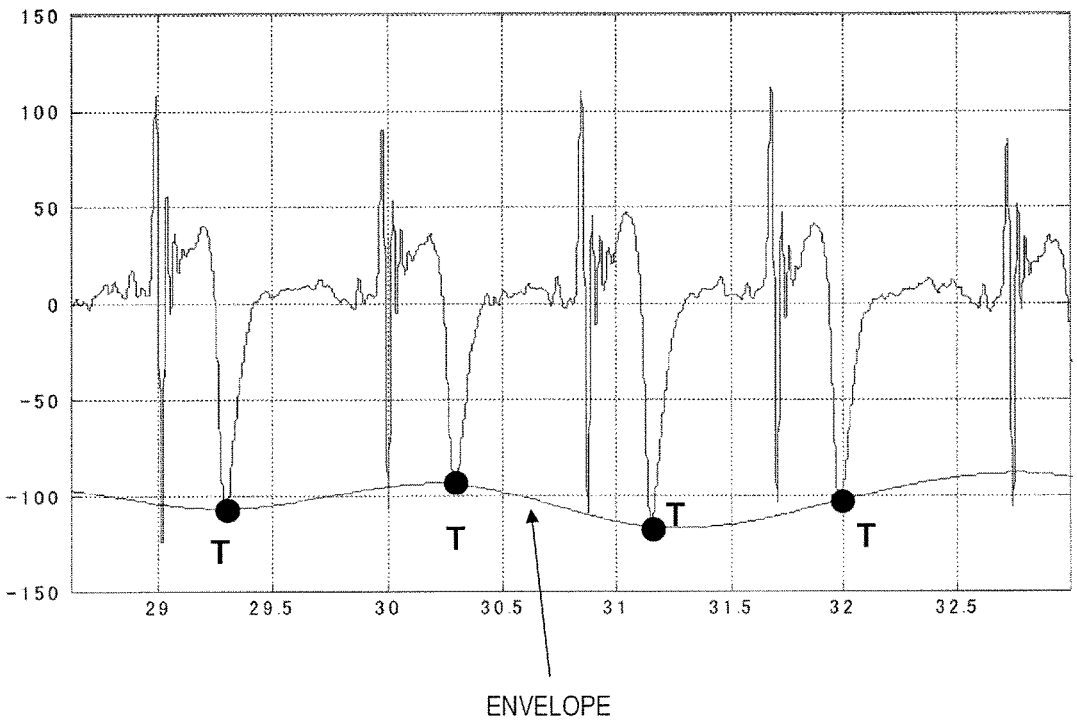
FIG. 12 is a diagram showing an exemplary envelope of T wave peaks.

The envelope generator 8 generates an envelope of the specific peaks (T wave peaks) detected at step S40. In order to derive the envelope, the envelope generator 8 according to the present embodiment interpolates between T wave peaks with a spline curve. The envelope generator 8 determines an envelope which smoothly interconnects the peaks by using a cubic spline curve, for example. Note that an $n^{th}$ spline curve refers to a curve whose $0^{th}$ order to $n-1^{th}$ order derivatives are continuous at all points. FIG. 12 shows an exemplary envelope of T wave peaks.

<Step S60>

The respiratory output unit 9 outputs information of the envelope generated at step S50 as a respiratory component. The mode of output may be displaying on a screen or the like, or recording onto a storage medium.

Next, the details of the wave peak detection process of step S40 above will be described.

As shown in FIG. 1A, among the P wave, Q wave, R wave, S wave, and T wave, which are the fundamental electrocardiographic components, peaks defining the P wave, R wave, and T wave are local minimums, whereas peaks defining the Q wave and S wave are local maximums. Although these peaks may somewhat fluctuate in level, the general tendency of the peaks defining the P wave, R wave, and T wave is that P wave peaks are relatively small, and that R wave and T wave peaks are larger than P wave peaks. Therefore, threshold processing is applied to a plurality of local minimums of the waveform. Specifically, if a plurality of local minimums of the waveform are equal to or less than a predetermined threshold value, those local minimums are supposed to indicate either R wave peaks or T wave peaks. In the present embodiment, the predetermined threshold value is −16 μV. Note that the choice of the exact predetermined threshold value is closely related to the measurement method of thoracic impedance. The aforementioned specific predetermined threshold value is only an example.

In order to distinguish whether a local minimum is an R wave peak or a T wave peak, the inventors employed the following method.

Figure 13:
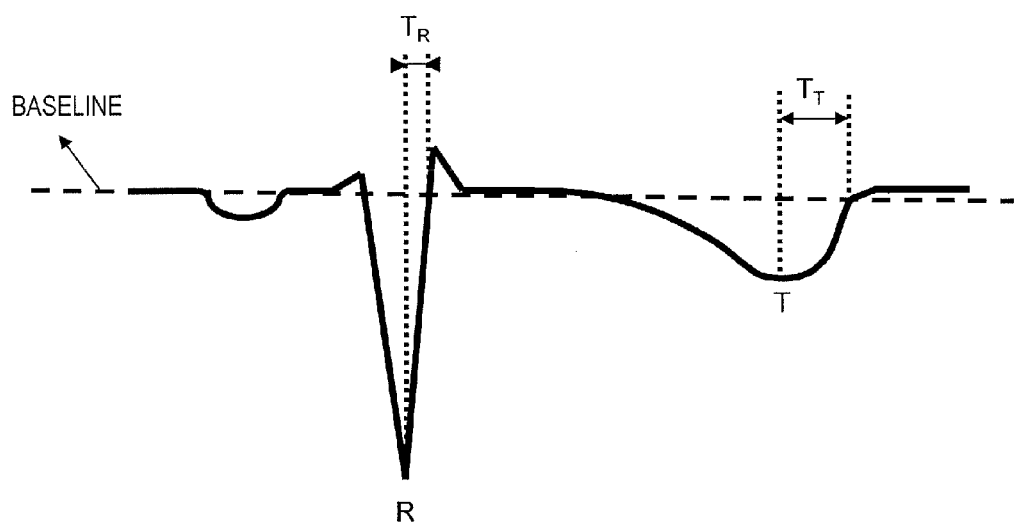
FIG. 13 is a diagram showing a method of distinction between a T wave peak and an R wave peak.

FIG. 13 shows a method of distinction between a T wave peak and an R wave peak. First, the time from the point in time of a local minimum until the impedance data returns to a predetermined baseline is calculated. That time will be designated as $T_R$ for an R wave, and $T_T$ for a T wave. Since a T wave has a greater time span than does an R wave, eq. (1) below holds.

$$T_T > T_R \qquad \text{eq. (1):}$$

Therefore, if the period of time from a point in time when a given local minimum is obtained until the impedance data returns to the predetermined baseline is equal to or greater than a predetermined value, that local minimum is regarded as a T wave. In the present embodiment, the baseline is −16 µV, and the predetermined value is 0.02 seconds.

Note that the threshold value used in detecting a local minimum which is a T wave peak may be changed based on the current value which is applied by the current-application unit 4.

Figure 14:
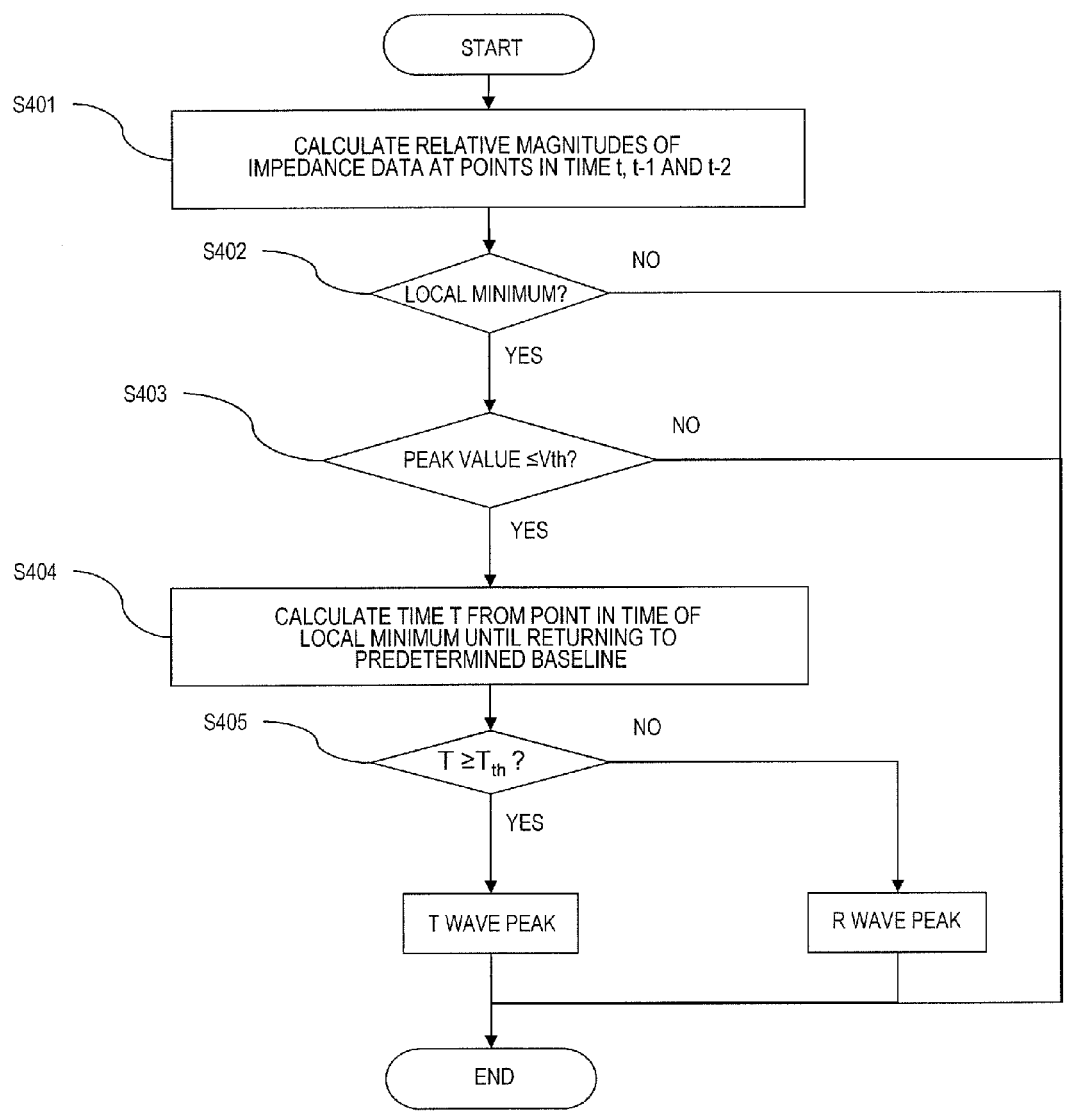
FIG. 14 is a flowchart showing a flow of processes of T wave peak detection.

FIG. 14 shows a flow of processes of T wave peak detection.

<Step S401>

The ECG component feature detector 7 calculates relative magnitudes of the impedance data which were measured at points in time t, t−1, and t−2.

<Step S402>

From the relative magnitudes calculated at step S401, the ECG component feature detector 7 determines the presence or absence of a local minimum. If a local minimum exists, the process proceeds to step S403. If no local minimum exists, the ECG component feature detector 7 determines that there is no T wave peak, and ends the process.

<Step S403>

If step S402 finds that a local minimum exists, the ECG component feature detector 7 determines whether the value of that peak is equal to or less than a predetermined threshold value (Vth). If the peak value is equal to or less than the predetermined threshold value, the process proceeds to step S404. If it is not equal to or less than the predetermined threshold value, the ECG component feature detector 7 determines that the local minimum is not a T wave peak, and ends the process.

<Step S404>

If step S403 finds that the peak value is equal to or less than the predetermined threshold value, the ECG component feature detector 7 calculates a time T from the point in time of the local minimum until returning to the predetermined baseline.

<Step S405>

The ECG component feature detector 7 determines whether the time T calculated at step S404 is equal to or greater than a predetermined value (Tth). If the time T is equal to or greater than the predetermined threshold value, the ECG component feature detector 7 determines that the local minimum is a T wave peak, and ends the process. If it is not equal to or greater than the predetermined threshold value, the ECG component feature detector 7 determines that the local minimum is an R wave peak, i.e., not a T wave peak, and ends the process.

In the present embodiment, a standard deviation of impedance which is measured in the recent 5 seconds is used as the predetermined threshold value (Vth). However, this is an example. A predetermined fixed value may be used as the threshold value. Alternatively, the threshold value may be changed based on the current value which applied by the current-application unit 4.

Through the above processes, a local minimum is determined to be a T wave peak or an R wave peak. Since this allows T wave peaks to be properly distinguished from R wave peaks, it is possible to properly detect T wave peaks as the aforementioned "specific peaks".

Figure 15:
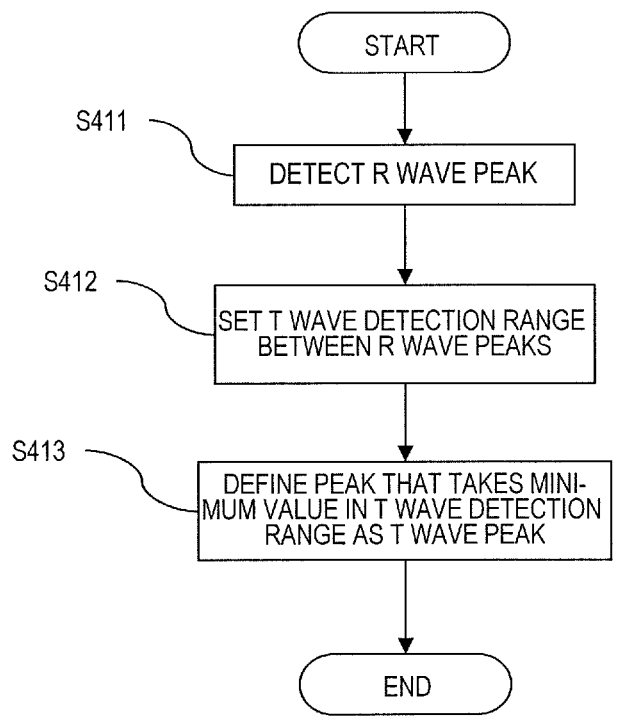
FIG. 15 is a flowchart showing another flow of processes of T wave peak detection.

Note that T wave peak detection may be performed by a method illustrated from steps S411 to S413 in FIG. 15. The flow of processes thereof is as follows.

<Step S411>

The ECG component feature detector 7 utilizes impedance data to detect R wave peaks. As the method of R wave peak detection, the process shown in FIG. 14, i.e., the process leading to "No" at step S405 in FIG. 14, is employed.

<Step S412>

Figure 16:
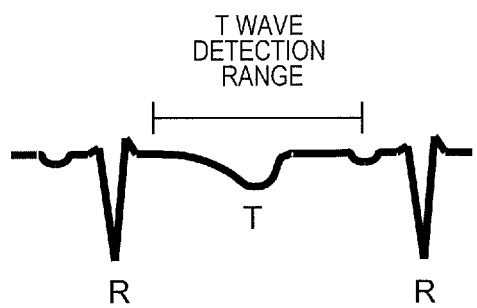
FIG. 16 is a diagram showing a T wave detection range between two adjacent R wave peaks.

The ECG component feature detector 7 sets a T wave detection range between two adjacent R wave peaks that have been detected at step S411. FIG. 16 shows a T wave detection range between two adjacent R wave peaks. In order to set a T wave detection range, the point in time $t_{R1}$ of the earlier-detected R wave peak (first R wave peak) and the point in time $t_{R2}$ of the later-detected R wave peak (second R wave peak) are used. For example, the T wave detection range t is set according to eq. (2) below.

$$t_{R1}+0.1 \leq t \leq t_{R2}-0.1 \qquad \text{eq. (2):}$$

<Step S413>

In the T wave detection range which was set at step S412, the ECG component feature detector 7 looks for a peak that takes the minimum value, and regards that minimum value as a T wave peak. Another way of looking at this process may be that the ECG component feature detector 7 acquires as a T wave peak a peak of the largest amplitude that is contained between adjacent R wave peaks.

(Results of Extraction for Respiratory Component)

FIGS. 17A to 17D show results of ascertaining a respiratory component by utilizing an envelope of T waves, with respect to thoracic impedance which is measured with a sine wave current of ±10 nA. FIG. 17A shows measured thoracic impedance, and FIG. 17B shows an extracted respiratory component. During measurement, the test subject was asked to consecutively undergo four manners of respiration:

Phase 1: 15 cycles of respiration with a period of 2 seconds (normal breathing)

Phase 2: 8 cycles of respiration with a period of 4 seconds (deep breathing)

Phase 3: suspended respiration

Phase 4: 14 cycles of respiration with a period of 2 seconds (normal breathing).

FIG. 17C is a bar chart showing an arithmetic mean and a standard deviation of amplitude in each phase. FIG. 17D shows values of arithmetic mean and standard deviation of amplitude in each phase. As shown in FIG. 17B, the actual respiratory rate and the number of peaks correspond in all but Phase 3. In Phase 3, too, because of its small amplitude, any amplitude which is equal to or less than a predetermined threshold value may be determined as pointing to a suspended respiration state. There is correlation between amplitude and actual respiratory volume, and the standard deviation of amplitude is small. Thus, it is indicative that a respiratory component can be correctly extracted by using an envelope of T waves with respect to thoracic impedance which is measured with a current of 10 nA.

Comparative Example is shown in FIGS. 18A to 18D. FIGS. 18A to 18D show results of ascertaining a respiratory component by utilizing an envelope of R waves, with respect to thoracic impedance which is measured with a current of 10 nA. As shown in FIG. 18B, it can be understood that the actual respiratory rate and the number of peaks do not correspond. Although there is correlation between amplitude and actual respiratory volume, the large standard deviation detracts from reliability.

FIGS. 19A to 19D and FIGS. 20A and 20B show results of output by the respiratory output unit 9 (example displays on a screen). FIG. 19A shows an example display in graph form. Three graphs are being displayed. In these graphs, the horizontal axis represents time, whereas the vertical axis represents heart rate, respiratory rate, and respiratory volume, respectively. FIG. 19B shows an example display in graph form. The horizontal axis represents time, whereas the vertical axis represents an electrocardiogram waveform and a respiration waveform, respectively. FIG. 19C shows an example display in the form of numerical values. Heart rate, respiratory rate, and respiratory volume are indicated. FIG. 19D shows an example where a bar representing the state of respiration (Respiration bar) is displayed. As the user breathes in, the bar extends in length ("Inhale"). As the user breathes out, the bar shrinks in length ("Exhale").

Figure 20A:
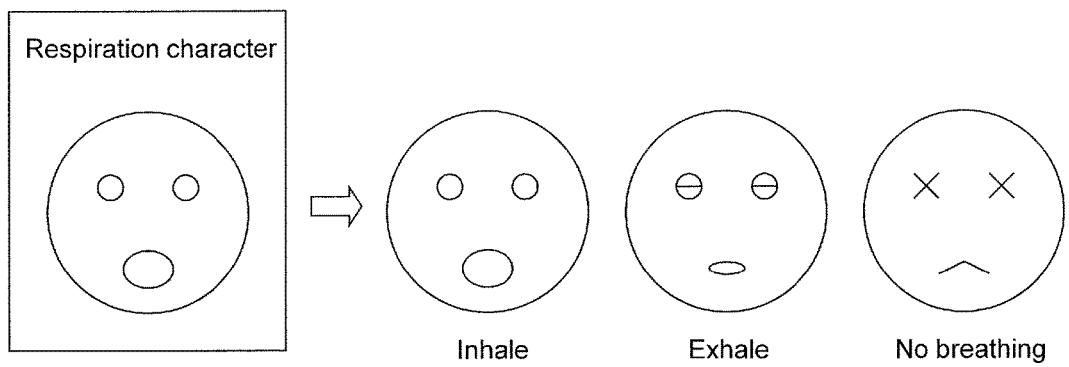
FIGS. 20A and 20B are diagrams showing example displays made by the respiratory output unit 9 on a screen.
Figure 20B:
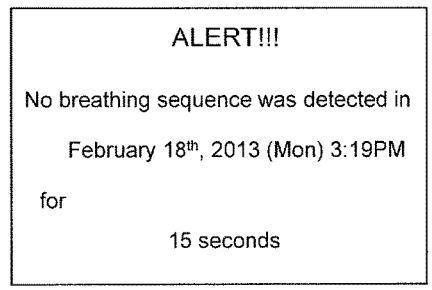

FIG. 20A shows an example display based on a character which represents the state of respiration. Depending on whether the user is breathing in, breathing out, or not undergoing any respiration (i.e., apnea), the character changes its facial expression. FIG. 20B shows an example alert display when apnea is detected. The point in time of detecting apnea and the period of time during which apnea occurred are displayed.

In the above examples, it is assumed that the applied current value is 10 nA. Hereinafter, with reference to FIG. 21 and FIG. 22, the range of current value to be applied in which the above-described respiratory component extraction process will be valid is discussed.

Figure 21:
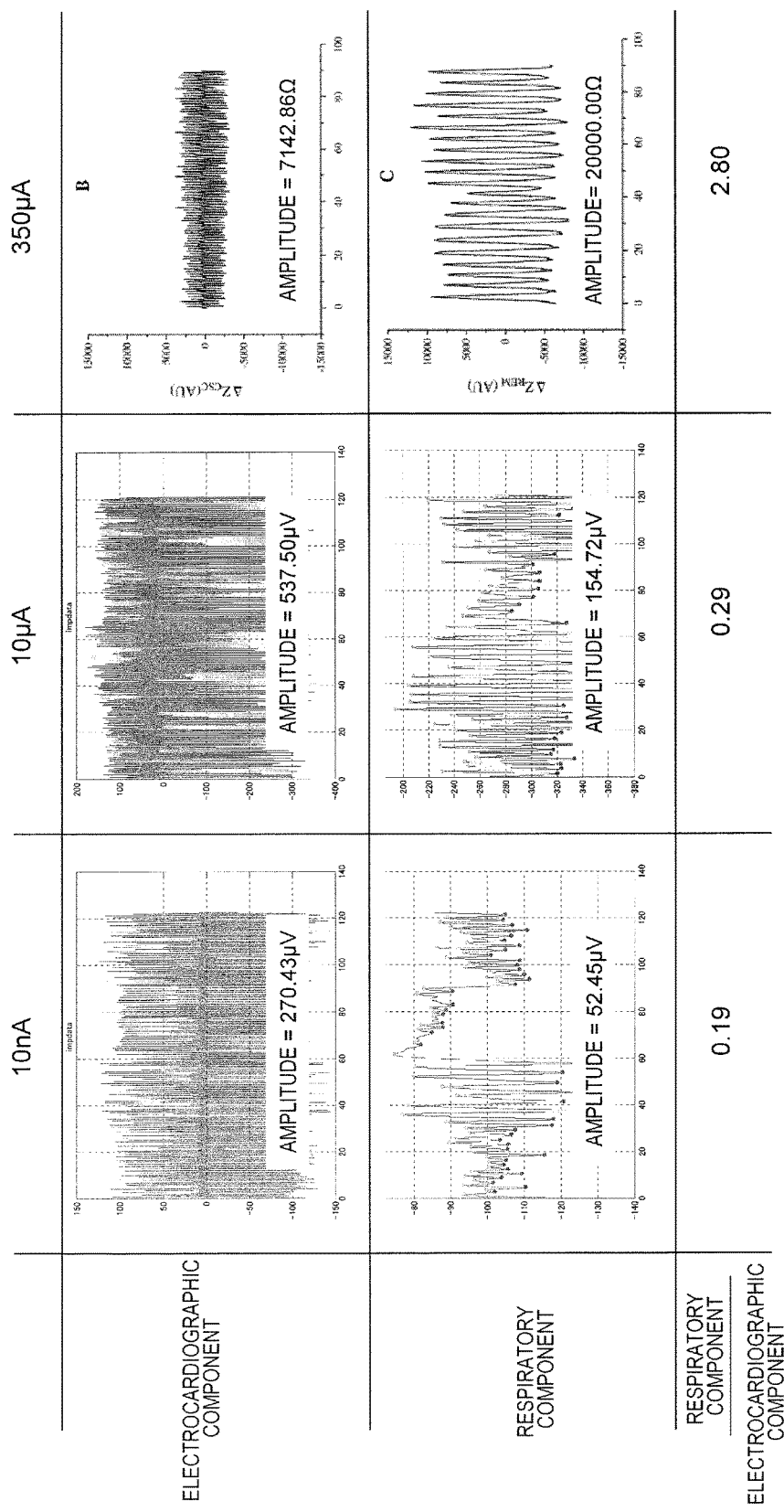
FIG. 21 is a diagram showing ratios between the respiratory component and the electrocardiographic component of a thoracic impedance, where measurements are taken with various current values.

FIG. 21 shows ratios between the respiratory component and the electrocardiographic component in thoracic impedance, where measurements are taken with various current values.

In the cases where the current value is 10 nA and 10 μA, the respiratory component is smaller than the electrocardiographic component. This means that the value of respiratory component/electrocardiographic component is 1 or less. FIG. 21 shows the measured values and the like.

On the other hand, as has been mentioned earlier, the respiratory component is greater than the electrocardiographic component when the current value is 350 μA. Therefore, the value of (respiratory component/electrocardiographic component) is 2.80.

The aforementioned respiratory component extraction process is considered sufficiently valid when the value of (respiratory component/electrocardiographic component) is 1 or less.

Figure 22:
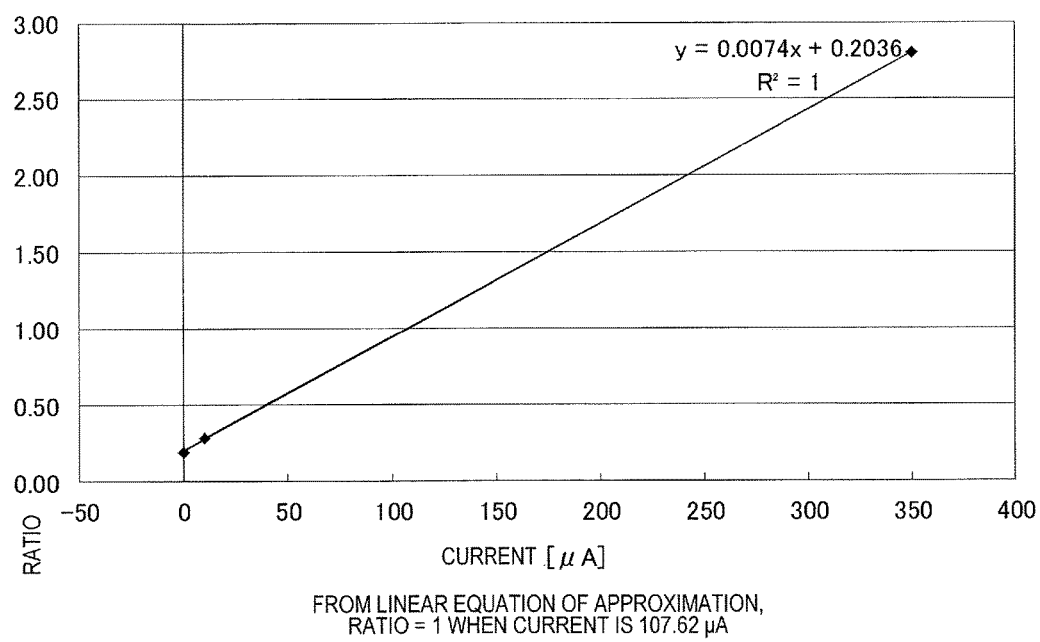
FIG. 22 is a diagram showing a current value, as determined by linear approximation with respect to exemplary cases of 10 nA and 10 µA, where respiratory component/electrocardiographic component equals 1.

FIG. 22 shows a current value, as determined by linear approximation with respect to the exemplary cases of 10 nA and 10 μA, where the value of (respiratory component/ electrocardiographic component) equals 1. The current value in this case was 107.62 μA. It is considered that the respiratory component extraction process according to the present embodiment is valid when the current value of the applied current is at least 10 nA or more, and particularly valid when the current value is 107.62 μA or less.

With the above-described construction and processes, respiration can be extracted from a thoracic impedance which is measured with a low current on the order of several nA, thus enabling measurement of an electrocardiogram and respiration in a simple manner, in a battery-driven mobile device which has a long battery run time.

(Embodiment 2)

In the present embodiment, a respiratory rate of the user 1 is estimated with respect to a respiratory component which is output from the respiratory output unit 9.

(Biological Signal Measurement System Construction)

Figure 23:
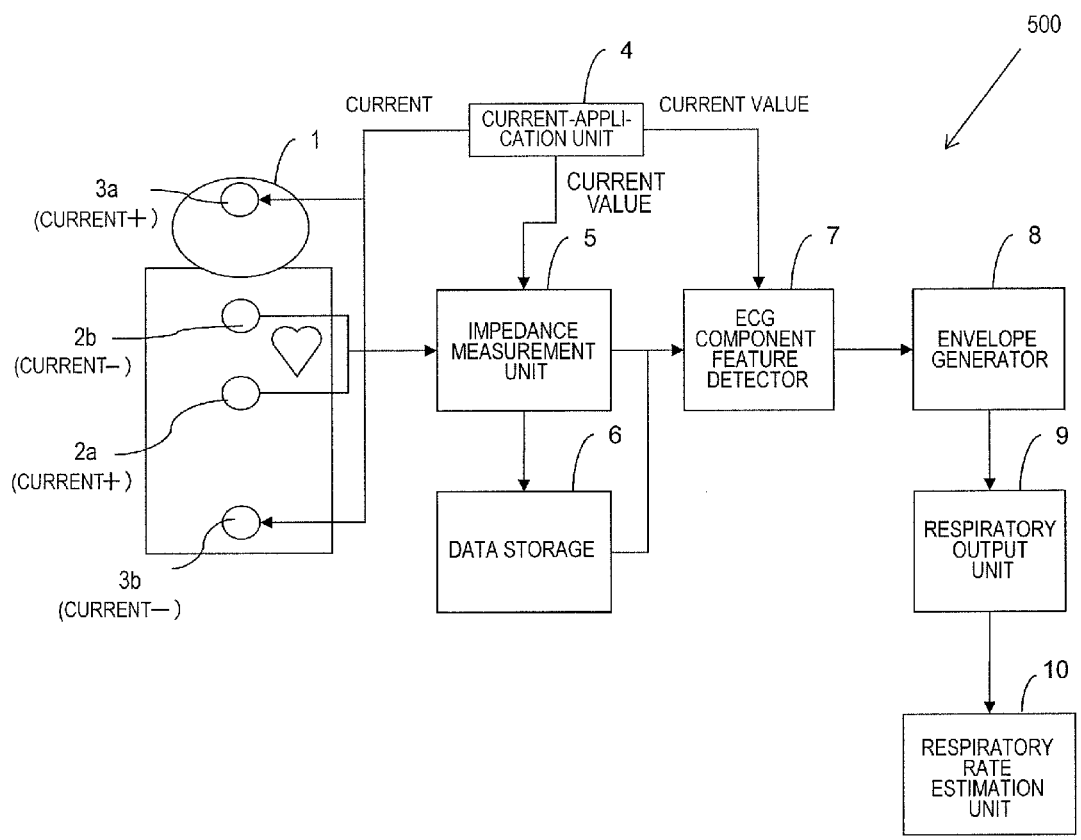
FIG. 23 is a diagram showing the construction of a biological information measurement system 500 according to Embodiment 2.

FIG. 23 shows the construction of a biological information measurement system 500 according to the present embodiment.

A difference between the biological information measurement system 500 of the present embodiment and the biological information measurement system 100 of Embodiment 1 is that the biological information measurement system 500 further includes a respiratory rate estimation unit 10. Note that the present system 500 is also of the construction shown in FIG. 7, although the data storage 6, the biological signal measurement apparatus 200, and the biological information computation apparatus 300 are not as distinguishably shown in FIG. 23 as in FIG. 7, this being for convenience of illustration. For example, the respiratory rate estimation unit 10 is to be provided in the biological information computation apparatus 300.

(Overall Flow of Processes)

Figure 24:
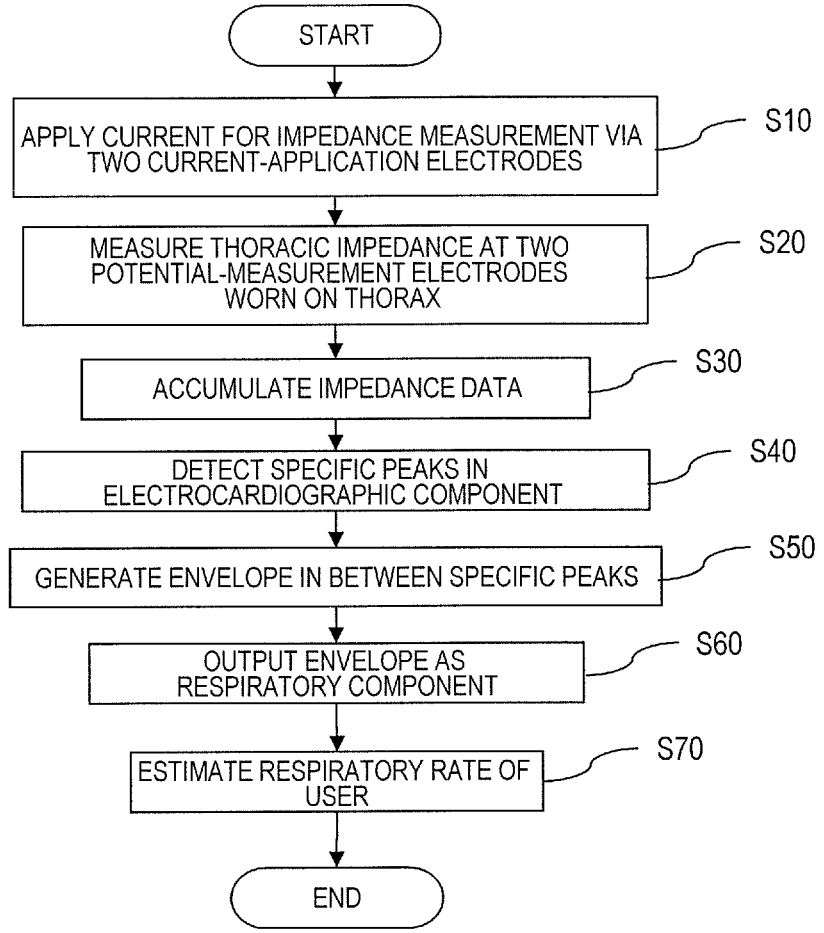
FIG. 24 is a flowchart showing an overall flow of processes by the biological information measurement system 500 according to Embodiment 2.

FIG. 24 shows an overall flow of processes by the biological information measurement system 500 of the present embodiment. Steps S10 to S60 are identical to the flow of processes in Embodiment 1, and therefore are omitted from description herein.

<Step S70>

From a respiratory component which is output at step S60, the respiratory rate estimation unit 10 estimates a respiratory rate of the user 1. The details of this process will be described with reference to FIG. 25.

(Flow of Processes of Respiratory Rate Estimation)

In order to accommodate changes in the respiration of the user 1, the respiratory rate estimation unit 10 estimates a respiratory rate at every fixed time interval. In the present embodiment, the respiratory rate is estimated at a time interval of 1 second.

Figure 25:
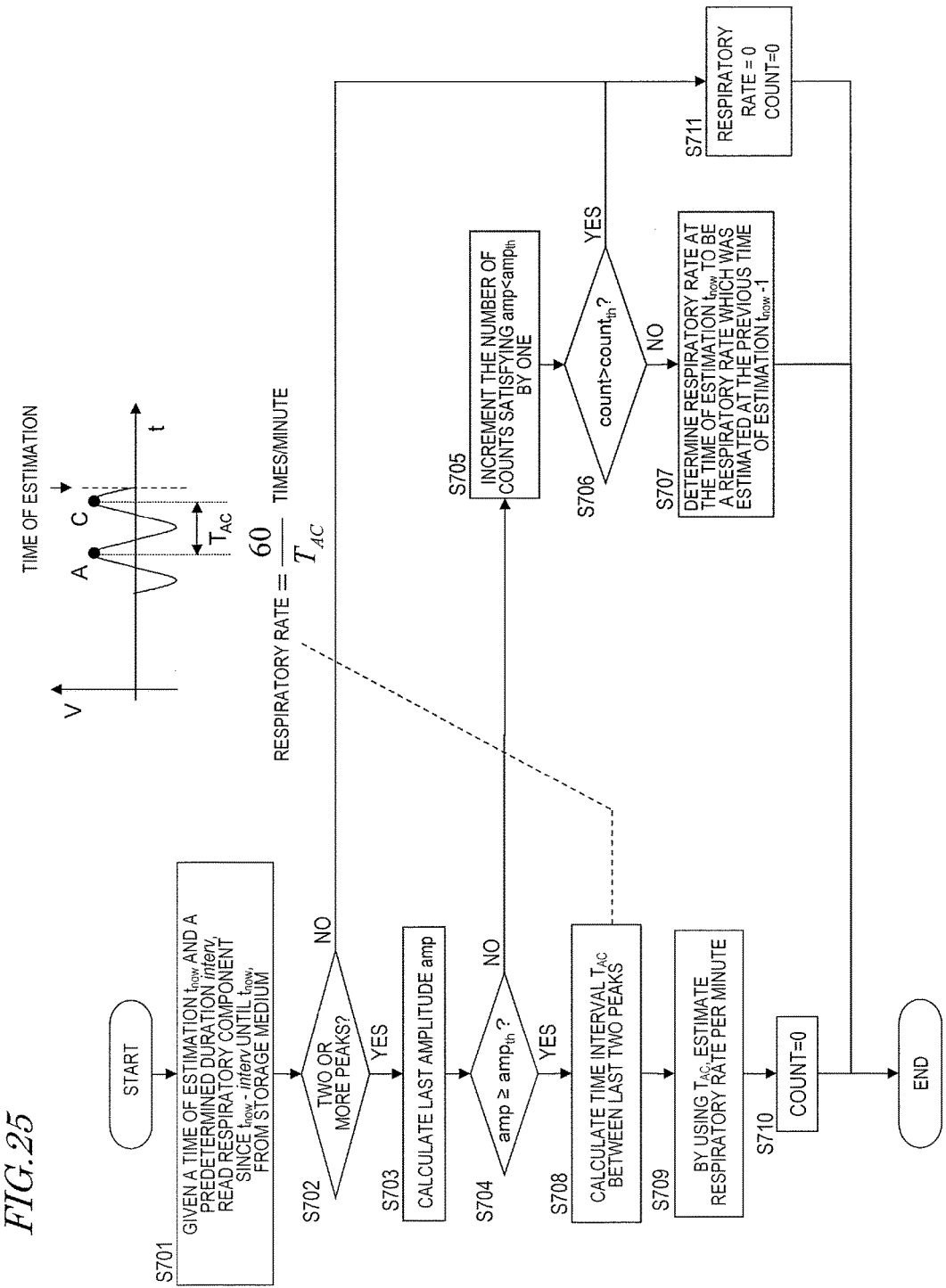
FIG. 25 is a flowchart showing a flow of processes of respiratory rate estimation on a time of estimation-by-time of estimation basis.

FIG. 25 shows a flow of processes of respiratory rate estimation on a time of estimation-by-time of estimation basis. In the following description, the terms "peak" and "bottom" refer to, respectively, a local maximum and a local minimum in a respiratory component.

<Step S701>

Given a time of estimation $t_{now}$ and a predetermined duration interv, the respiratory rate estimation unit 10 reads a respiratory component since $t_{now}$−interv until $t_{now}$, from the storage medium. In other words, data of the respiratory component is read as indicated by eq. (3) below.

$$t_{now}\text{−interv} \leq t \leq t_{now} \qquad \text{eq. (3):}$$

In the present embodiment, the predetermined duration interv is 10 seconds.

<Step S702>

The respiratory rate estimation unit 10 determines whether two or more peaks exist in the respiratory component which was read at step S701. If two or more peaks exist, the process proceeds to step S703. If not, the process proceeds to step S711.

<Step S703>

The respiratory rate estimation unit 10 calculates the last amplitude amp of the respiratory component. The "last amplitude" refers to a potential (impedance) difference between the latest peak and the latest bottom.

<Step S704>

The respiratory rate estimation unit 10 determines whether the last amplitude amp calculated at step S703 is equal to or greater than a predetermined threshold value $amp_{th}$. If it is equal to or greater than the predetermined threshold value $amp_{th}$, the process proceeds to step S708. If not, the process proceeds to step S705. In the present embodiment, $amp_{th}$ is 6.88 μV.

<Step S705>

The respiratory rate estimation unit 10 increments the number of counts for which the condition amp≥$amp_{th}$ has not been satisfied at step S704 by one.

<Step S706>

The respiratory rate estimation unit 10 determines whether the number of counts for which the condition amp≥$amp_{th}$ has not been satisfied at step S704 exceeds a predetermined threshold value $count_{th}$. In the present embodiment, count$_{th}$ is 1. If the predetermined threshold value count$_{th}$ is exceeded, the process proceeds to step S711. If not, the process proceeds to step S707.

<Step S707>

The respiratory rate estimation unit 10 determines the respiratory rate at the time of estimation t$_{now}$ to be a respiratory rate which was estimated at the previous time of estimation t$_{now}$−1. The respiratory rate estimation process is ended here.

<Step S708>

The respiratory rate estimation unit 10 calculates a time interval T$_{AC}$ between the last two peaks A and C.

<Step S709>

By using the T$_{AC}$ calculated at step S708, the respiratory rate estimation unit 10 estimates a respiratory rate per minute, according to eq. (4) below.

$$\text{respiratory rate} = \frac{60}{T_{AC}} [\text{times/minute}] \qquad \text{eq. (4)}$$

<Step S710>

The respiratory rate estimation unit 10 resets the number of counts of not satisfying the condition amp≥amp$_{th}$ at step S704. The respiratory rate estimation process is ended here.

<Step S711>

The respiratory rate estimation unit 10 resets the number of counts of not satisfying the condition amp≥amp$_{th}$ at step S704, while also setting the respiratory rate at 0. The respiratory rate estimation process ends at this process.

(Estimated Results for Respiratory Rate)

Figure 26:
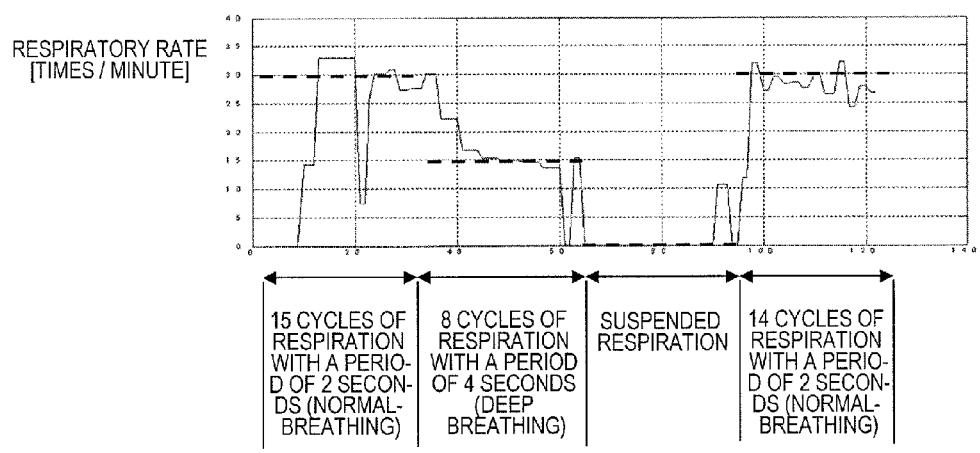
FIG. 26 is a diagram showing estimated results of respiratory rates.

FIG. 26 shows estimated results of respiratory rates. These results are obtained by using the results of extraction shown in FIG. 17B. Under respiration with a period of 2 seconds and respiration with a period of 4 seconds, the respiratory rate will ideally be 30 [times/minute] and 15 [times/minute], respectively. FIG. 26 indicates that a close value to that value is obtained for each phase.

With the above construction and processes, respiration can be extracted from a thoracic impedance which was measured with a low current on the order of several nA; a respiratory rate of the user can be estimated with respect to the extracted respiratory component; and the estimated respiratory rate can be presented to the user.

(Embodiment 3)

The biological signal measurement system of the present embodiment estimates a respiratory volume of the user 1 from the information of a respiratory component which is output from the respiratory output unit 9.

(Biological Signal Measurement System Construction)

Figure 27:
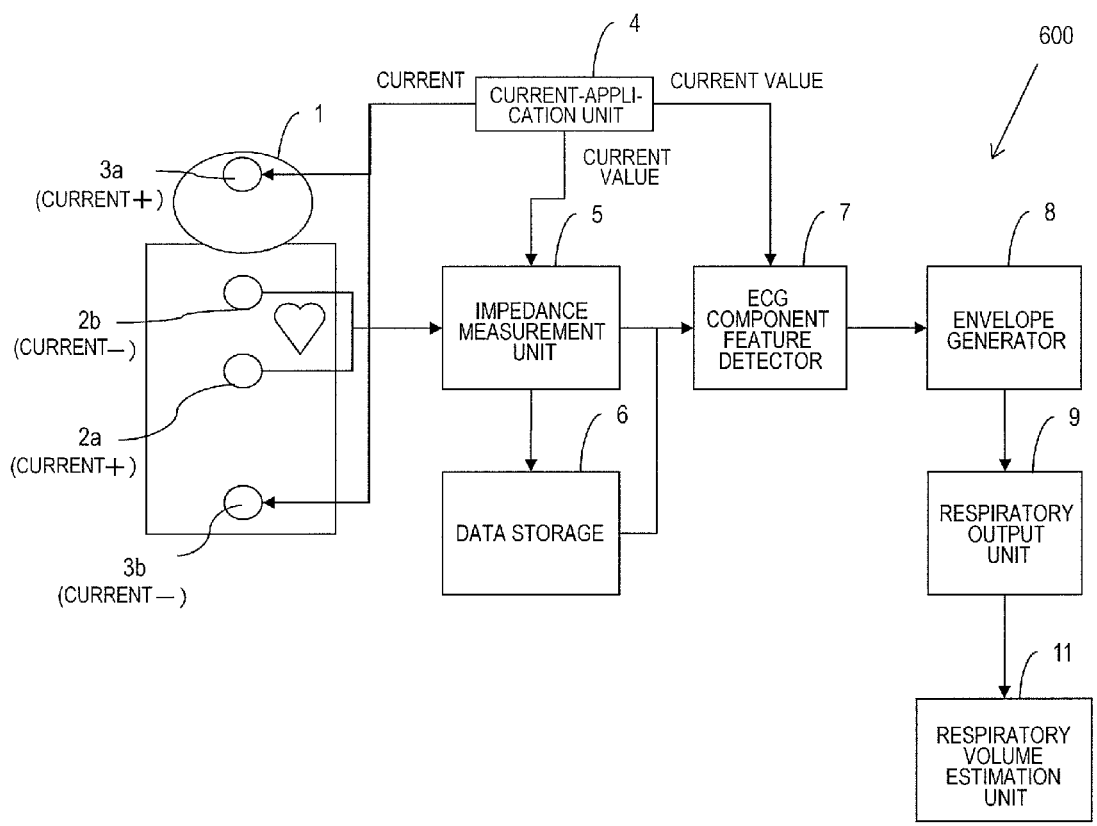
FIG. 27 is a diagram showing the construction of a biological information measurement system 600 according to Embodiment 3.

FIG. 27 shows the construction of a biological information measurement system 600 according to the present embodiment.

A difference between the biological information measurement system 600 of the present embodiment and the biological information measurement system 100 of Embodiment 1 is that the biological information measurement system 600 further includes a respiratory volume estimation unit 11. Note that the present system 600 is also of the construction shown in FIG. 7, although the data storage 6, the biological signal measurement apparatus 200, and the biological information computation apparatus 300 are not as distinguishably shown in FIG. 27 as in FIG. 7, this being for convenience of illustration. For example, the respiratory volume estimation unit 11 is to be provided in the biological information computation apparatus 300.

(Overall Flow of Processes)

Figure 28:
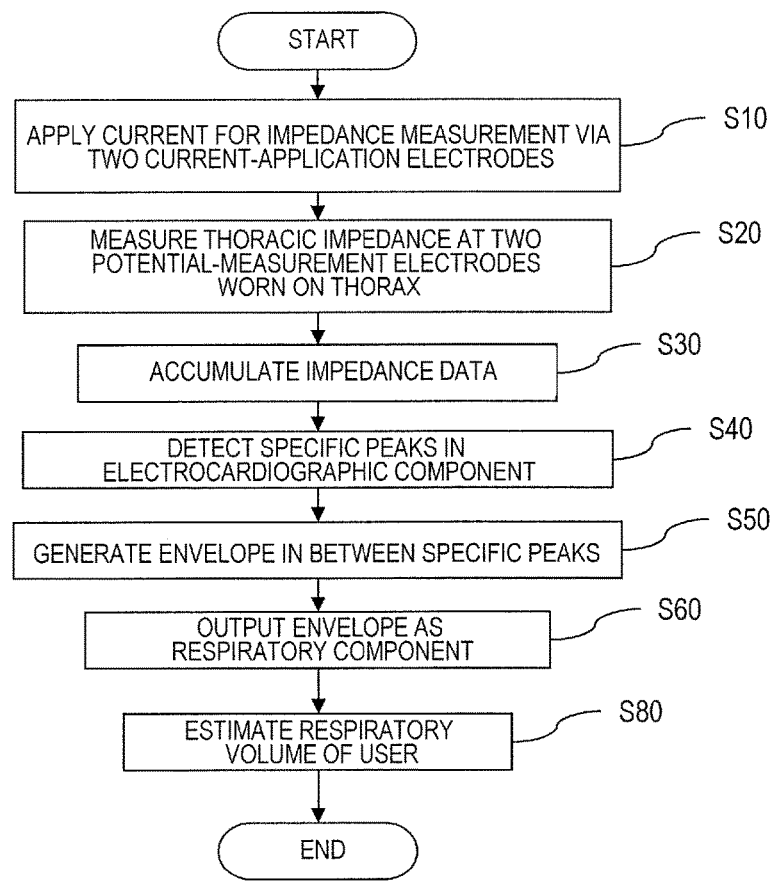
FIG. 28 is a flowchart showing an overall flow of processes by the biological information measurement system 600 according to Embodiment 3.

FIG. 28 shows an overall flow of processes by the biological information measurement system 600 of the present embodiment. Steps S10 to S60 are identical to the flow of processes in Embodiment 1, and therefore are omitted from description herein.

<Step S80>

From a respiratory component which was output at step S60, the respiratory volume estimation unit 11 estimates a respiratory volume of the user 1. The details of this process will be described with reference to FIG. 29.

(Flow of Processes of Respiratory Volume Estimation)

In order to accommodate changes in the respiration of the user 1, the respiratory volume estimation unit 11 estimates the respiratory volume at every fixed time interval. In the present embodiment, the respiratory volume is estimated at a time interval of 1 second.

Figure 29:
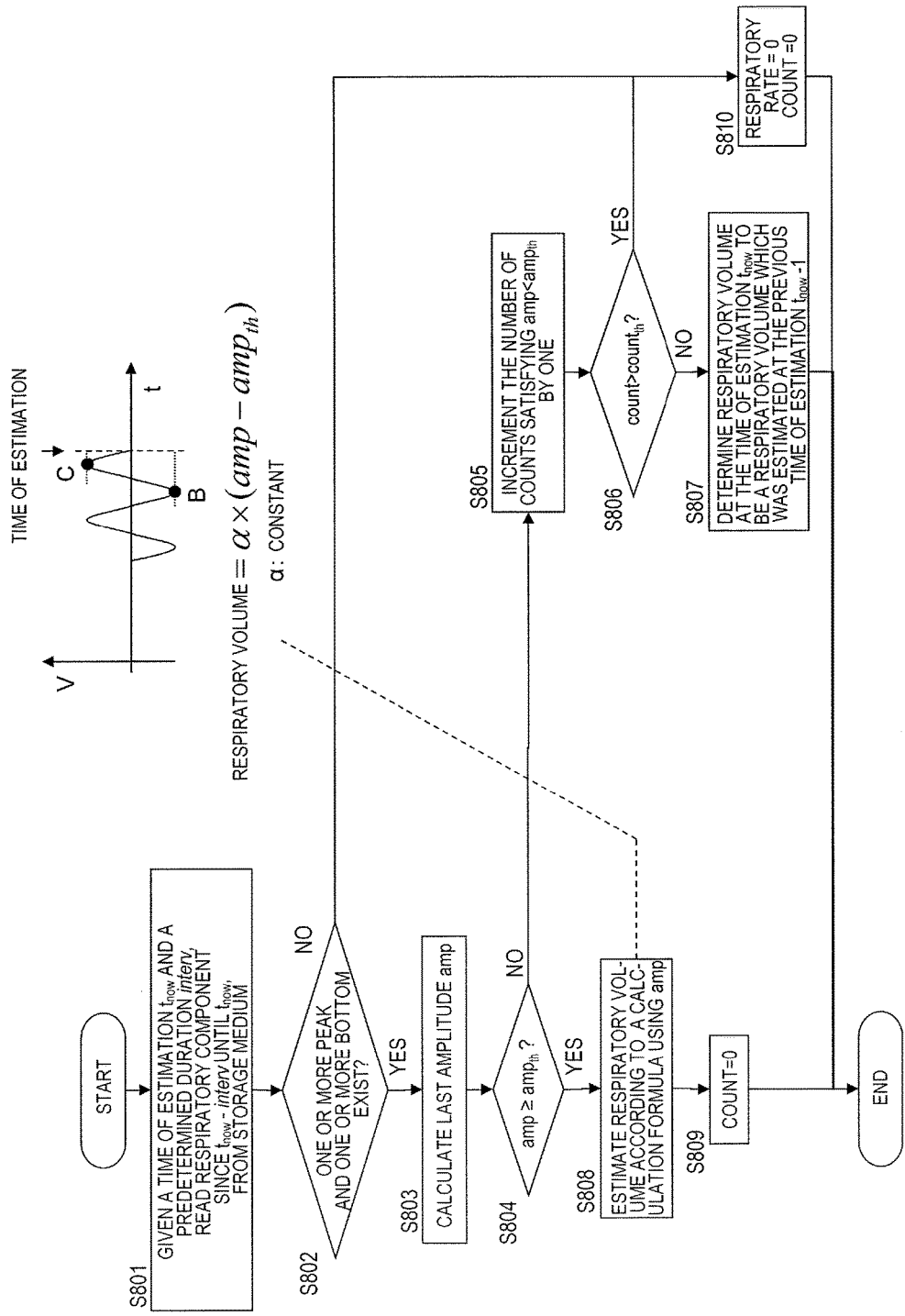
FIG. 29 is a flowchart showing a flow of processes of respiratory volume estimation on a time of estimation-by-time of estimation basis.

FIG. 29 shows a flow of processes of respiratory volume estimation on a time of estimation-by-time of estimation basis. In the following description, the terms "peak" and "bottom" refer to, respectively, a local maximum and a local minimum in a respiratory component.

<Step S801>

Given a time of estimation t$_{now}$ and a predetermined duration interv, the respiratory volume estimation unit 11 reads a respiratory component since t$_{now}$−interv until t$_{now}$, ≤from the storage medium. In other words, data of the respiratory component is read as indicated by eq. (5) below.

$$t_{now}\text{−interv} \le t \le t_{now} \qquad \text{eq. (5):}$$

In the present embodiment, the predetermined duration interv is 10 seconds.

<Step S802>

The respiratory volume estimation unit 11 determines whether one or more peak and one or more bottom exist in the respiratory component which was read at step S801. If one or more peak and one or more bottom exist, the process proceeds to step S803. If not, the process proceeds to step S810.

<Step S803>

The respiratory volume estimation unit 11 calculates the last amplitude amp of the respiratory component. The "last amplitude" refers to a potential (impedance) difference between the latest peak and the latest bottom.

<Step S804>

The respiratory volume estimation unit 11 determines whether the last amplitude amp calculated at step S803 is equal to or greater than a predetermined threshold value amp$_{th}$. If it is equal to or greater than the predetermined threshold value amp$_{th}$, the process proceeds to step S808. If not, the process proceeds to step S805. In Embodiment 2, amp$_{th}$ is 6.88 μV.

<Step S805>

The respiratory volume estimation unit 11 increments the number of counts for which the condition amp≥amp$_{th}$ has not been satisfied at step S804 by one.

<Step S806>

The respiratory volume estimation unit 11 determines whether the number of counts for which the condition amp≥amp$_{th}$ has not been satisfied at step S804 exceeds a predetermined threshold value count$_{th}$. In the present embodiment, count$_{th}$ is 1. If the predetermined threshold value count$_{th}$ is exceeded, the process proceeds to step S810. If not, the process proceeds to step S807.

<Step S807>

The respiratory volume estimation unit 11 determines the respiratory volume at the time of estimation t$_{now}$ to be a respiratory volume which was estimated at the previous time of estimation $t_{now}-1$. The respiratory volume estimation process ends here.

<Step S808>

By using the last amplitude amp, the respiratory volume estimation unit 11 estimates a respiratory volume according to eq. (6) below.

$$\text{respiratory volume} = \alpha \times (\text{amp} - \text{amp}_{th}) \qquad \text{eq. (6):}$$

where $\alpha$ is a constant, which in the present embodiment is 1.

<Step S809>

The respiratory volume estimation unit 11 resets the number of counts of not satisfying the condition $\text{amp} \geq \text{amp}_{th}$ at step S804. The respiratory volume estimation process ends here.

<Step S810>

The respiratory volume estimation unit 11 resets the number of counts of not satisfying the condition $\text{amp} \geq \text{amp}_{th}$ at step S804, while also setting the respiratory volume at 0. The respiratory volume estimation process ends here.

(Estimated Results for Respiratory Volume)

Figure 30:
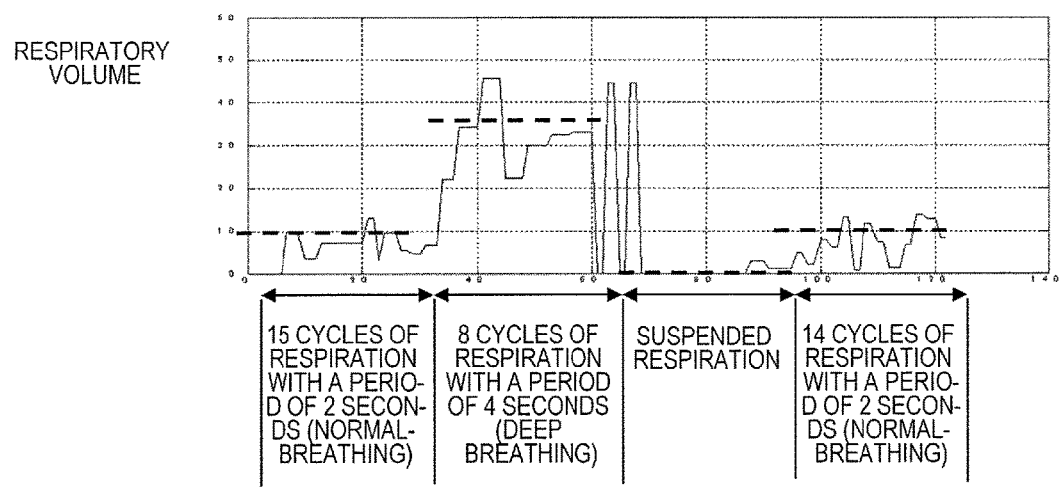
FIG. 30 is a diagram showing results of respiratory volume estimation made with respect to the results of extraction shown in FIG. 17B.

FIG. 30 shows results of respiratory volume estimation made with respect to the results of extraction shown in FIG. 17B. It can be seen that the estimated respiratory volume differs in each phase. The respiratory volume in Phase 2 (deep breathing) is greater than the respiratory volumes in Phase 1 (normal breathing) and Phase 4 (normal breathing). The respiratory volume in Phase 3 is almost zero.

With the above construction and processes, respiration can be extracted from a thoracic impedance which was measured with a low current on the order of several nA; a respiratory volume of the user can be estimated with respect to the extracted respiratory component; and the estimated respiratory volume can be presented to the user.

(Embodiment 4)

Figure 31A:
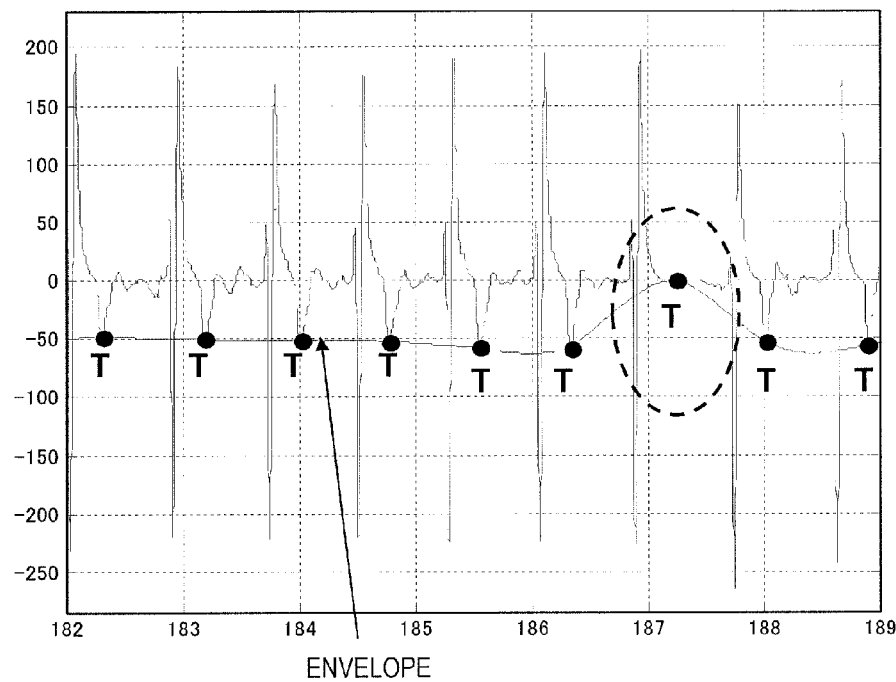
FIG. 31A is a diagram showing T wave measurement results.

FIG. 31A shows T wave measurement results. As shown in FIG. 31A, the measured thoracic impedance may occasionally lack a T wave, or contain a T wave peak whose amplitude is very small. If such a measured value is treated as a T wave in generating an envelope, the respiratory component will have an abrupt increase in amplitude, resulting in an incorrect respiratory component being generated. Therefore, if any such case occurs, the T wave needs to be calibrated.

In the biological signal measurement system according to the present embodiment, if a T wave which is detected by the ECG component feature detector 7 is smaller than a predetermined threshold value $\text{imp}_{th1}$, the T wave peak value is calibrated.

(Biological Signal Measurement System Construction)

Figure 32:
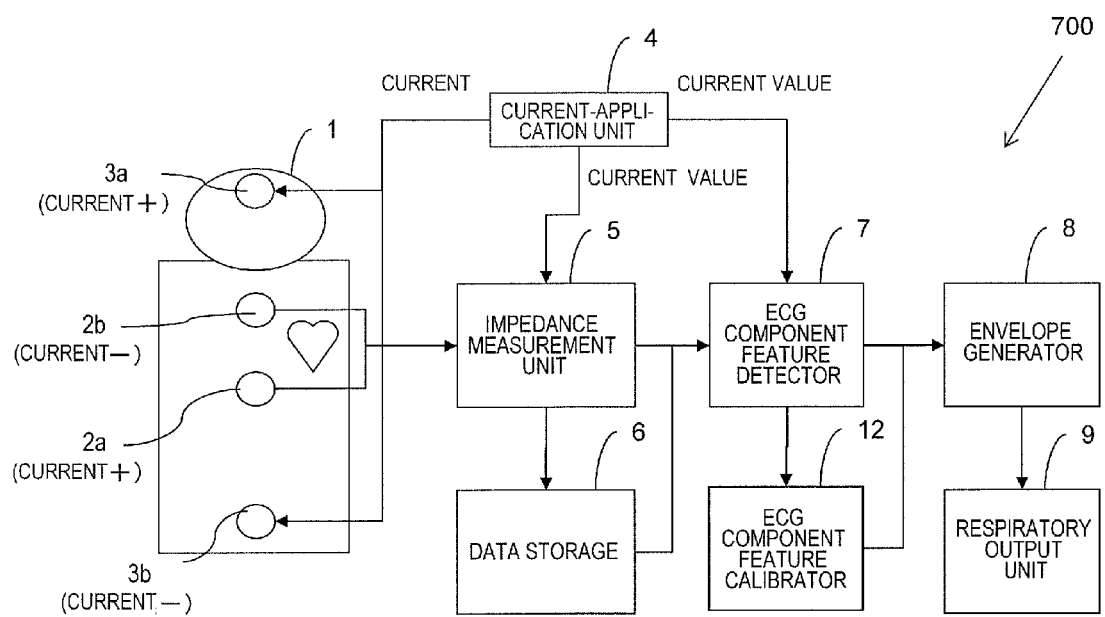
FIG. 32 is a diagram showing the construction of a biological information measurement system 700 according to Embodiment 4.

FIG. 32 shows the construction of a biological information measurement system 700 according to the present embodiment.

A difference between the biological information measurement system 700 of the present embodiment and the biological information measurement system 100 of Embodiment 1 is that the biological information measurement system 700 further includes an electrocardiographic component feature calibrator 12. Note that the present system 700 is also of the construction shown in FIG. 7, although the data storage 6, the biological signal measurement apparatus 200, and the biological information computation apparatus 300 are not as distinguishably shown in FIG. 32 as in FIG. 7, this being for convenience of illustration. For example, the electrocardiographic component feature calibrator 12 is to be provided in the biological information computation apparatus 300.

(Overall Flow of Processes)

Figure 33:
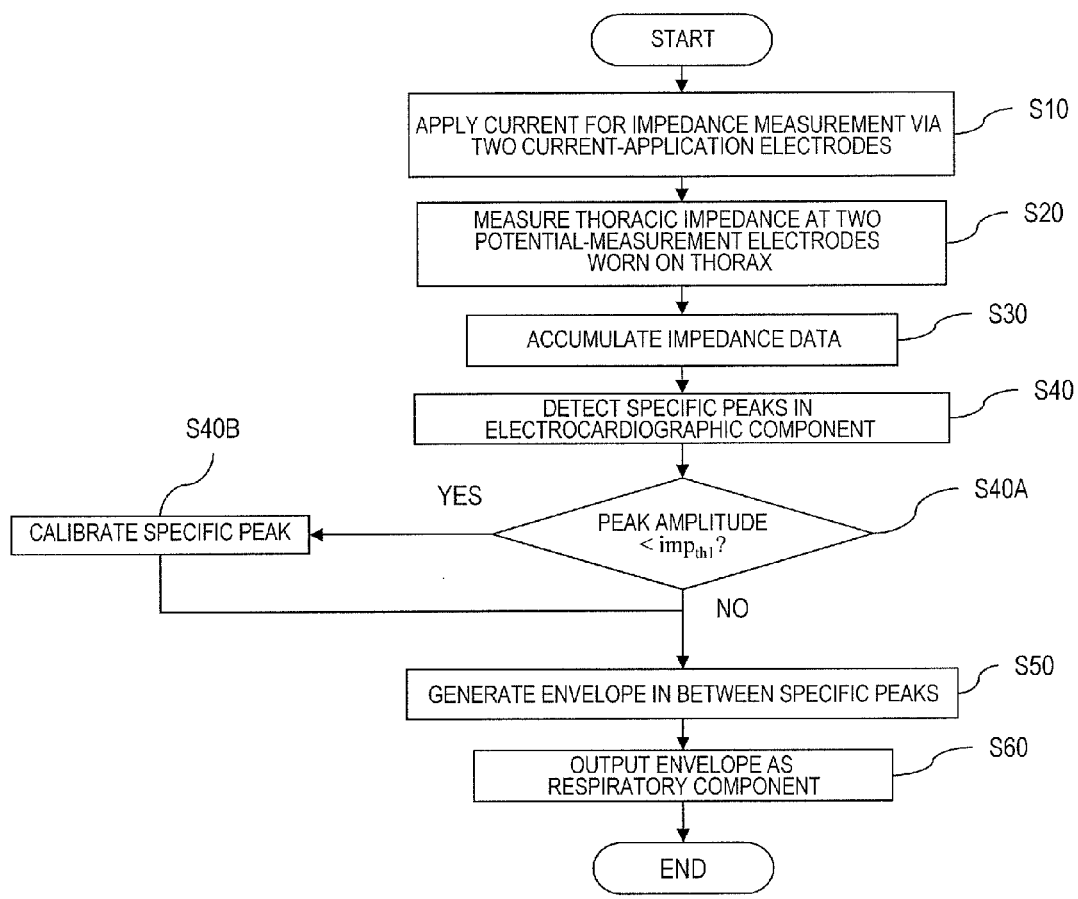
FIG. 33 is a flowchart showing overall flow of processes by the biological information measurement system 700 according to Embodiment 4.

FIG. 33 shows an overall flow of processes by the biological information measurement system 700 of the present embodiment. Steps S10 to S40 and steps S50 to S60 are identical to the flow of processes in Embodiment 1, and therefore are omitted from description herein.

<Step S40A>

The ECG component feature detector 7 determines whether a T wave peak value which was detected at step S40 is smaller than the threshold value $\text{imp}_{th1}$. If it is smaller, the process proceeds to step S40B. If not, the process proceeds to step S50. In the present embodiment, the threshold value $\text{imp}_{th1}$ is 5.00 µV.

<Step S40B>

If it is determined that the T wave peak value which was detected at step S40 is smaller than the threshold value $\text{imp}_{th1}$, the electrocardiographic component feature calibrator calibrates the T wave peak value. The details of the calibration will be described in the "flow of processes of T wave calibration" below. After the calibration, the process proceeds to step S50.

(Flow of Processes of T Wave Calibration)

Figure 34:
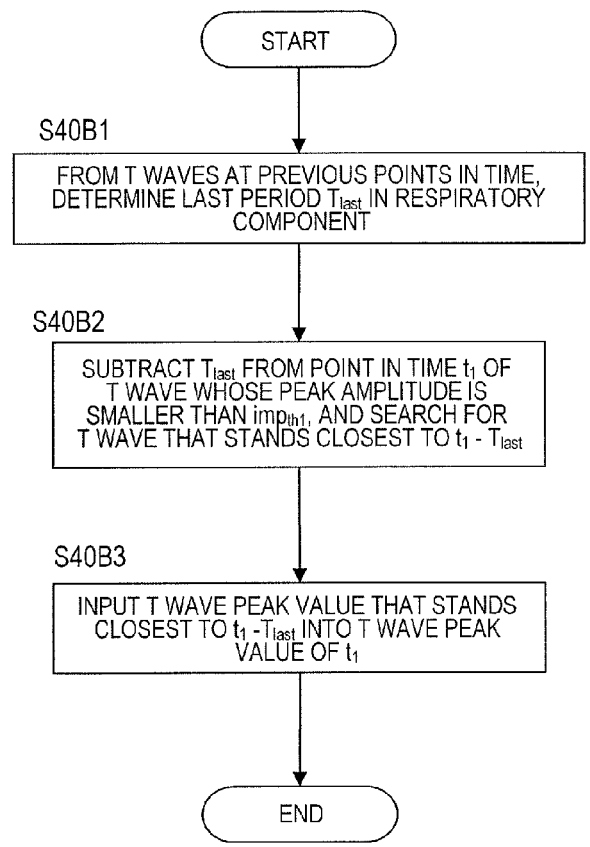
FIG. 34 is a flowchart showing a flow of processes of T wave calibration.

FIG. 34 shows a flow of processes of T wave calibration. The point in time of a T wave whose peak amplitude is smaller than $\text{imp}_{th1}$ is designated $t_1$.

<Step S40B1>

The electrocardiographic component feature calibrator 12 determines the last period $T_{last}$ in the respiratory component, from the T waves at previous points in time.

<Step S40B2>

The electrocardiographic component feature calibrator 12 subtracts the period $T_{last}$ from the point in time $t_1$, and searches for a T wave that stands closest to $(t_1 - T_{last})$.

<Step S40B3>

As a calibration value, the electrocardiographic component feature calibrator 12 inputs the T wave peak value that stands closest to $(t_1 - T_{last})$ into the T wave peak value at the point in time $t_1$.

Figure 35:
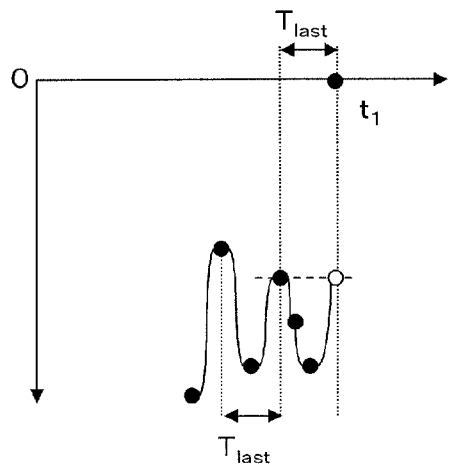
FIG. 35 is a diagram showing a calibration result.

FIG. 35 shows a calibration result. The topmost "●" represents a detected T wave peak. The "○" represents a result of calibrating the T wave peak. According to the present embodiment, the T wave peak ("●") which is detected at the point in time $t_1$ is calibrated to "○".

(T Wave Calibration Results)

Figure 31B:
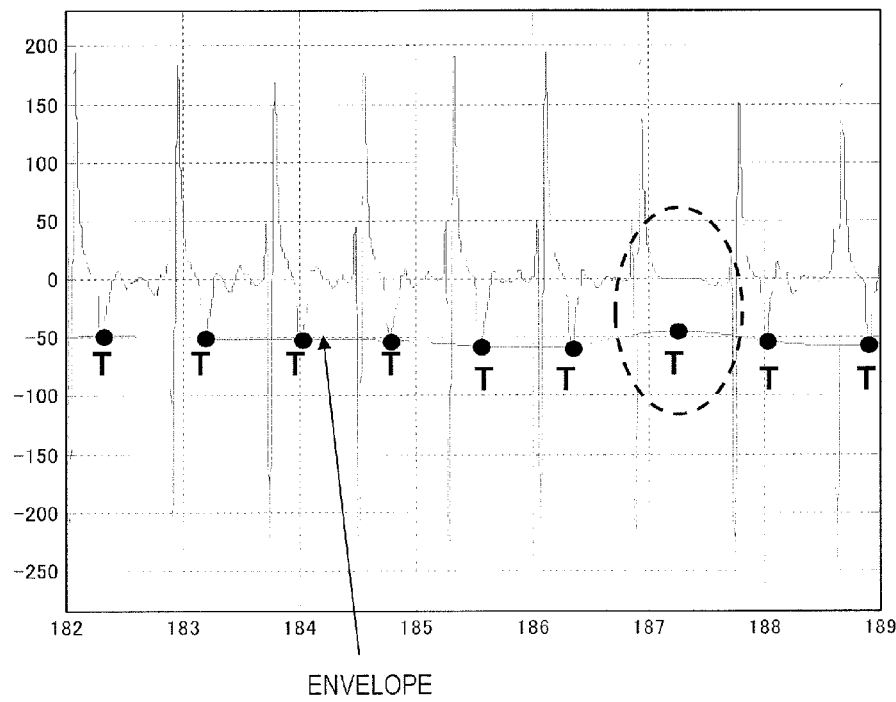
FIG. 31B is a diagram showing results of calibrating T waves from the waveform shown in FIG. 31A.

FIG. 31B shows a result of calibrating a T wave which is contained in the waveform shown in FIG. 31A. Even if there is a missing T wave, or a T wave peak whose amplitude is very small, calibration can prevent abrupt amplitude changes in the respiratory component.

With the above construction and processes, even if the measured thoracic impedance occasionally lacks a T wave, or contains a T wave peak whose amplitude is very small, the T wave peak can be calibrated, whereby a correct respiratory component can be extracted.

Thus, Embodiments 1 to 4 of the present disclosure have been described above.

Hereinafter, exemplary hardware constructions which are common to the biological information measurement systems of the above embodiments will be described. In the following description, an example construction is described in connection with the biological information measurement system 100 according to Embodiment 1.

Figure 36:
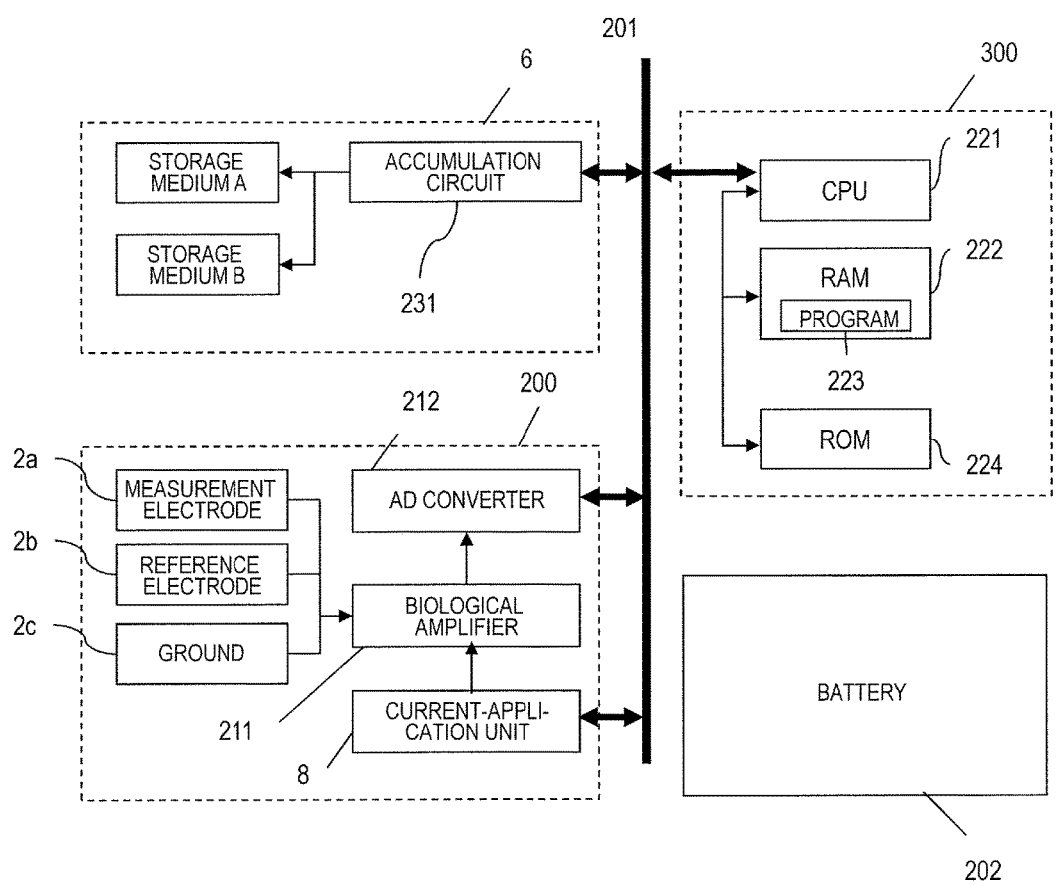
FIG. 36 is a diagram showing an exemplary hardware construction of a biological signal measurement system.

FIG. 36 shows an exemplary hardware construction of the biological signal measurement system 100. The data storage 6, the biological signal measurement apparatus 200, and the biological information computation apparatus 300 of the biological information measurement system 100 are interconnected via a bus 201, so that data exchange among them is possible. Moreover, power is supplied from the battery 202 to each circuit. Such hardware is stored in the housing of the biological signal measurement apparatus 200A, as shown in FIG. 8.

The biological signal measurement apparatus 200 includes a measurement electrode 2a, a reference electrode 2b, ground 2c, a biological amplifier 211, an AD converter 212, and a current-application unit 8. The biological amplifier 211 measures a potential difference and impedance between the measurement electrode 2a and the reference electrode 2b. When measuring impedance, the biological amplifier 211 takes the measurement while a weak current is flown from the current-application unit 8. Switching between potential measurement and impedance measurement is made under the control of the signal processing section 220. The measured data is converted from an analog signal into a digital signal by the AD converter 212, and sent to a CPU 221 of the signal processing section 220 via the bus 201.

The biological information computation apparatus 300 includes the CPU 221, a RAM 222, a program 223, and the ROM 224. The program 223 is to be stored in the RAM 222 or the ROM 224. The CPU 221 executes the program 223 stored in the RAM 222 or the ROM 224. In the program 223, a processing procedure according to any of the aforementioned flowcharts is described. In accordance with the computer program 223, the biological information computation apparatus 300 analyzes signals in the biological signal measurement apparatus 200, and store measurement data and results of analysis in the data storage 6.

The data storage 6 includes an accumulation circuit 231, storage medium A, and storage medium B. The data storage 6 records data which has been received from the signal processing section 22 to storage medium A or storage medium B, via the accumulation circuit. Storage medium A and storage medium B may be internalized flash memories, for example. Although FIG. 36 illustrates two kinds of storage media, this is an example. Two different regions of the same storage medium may be assigned as if two kinds of storage media.

Figure 37:
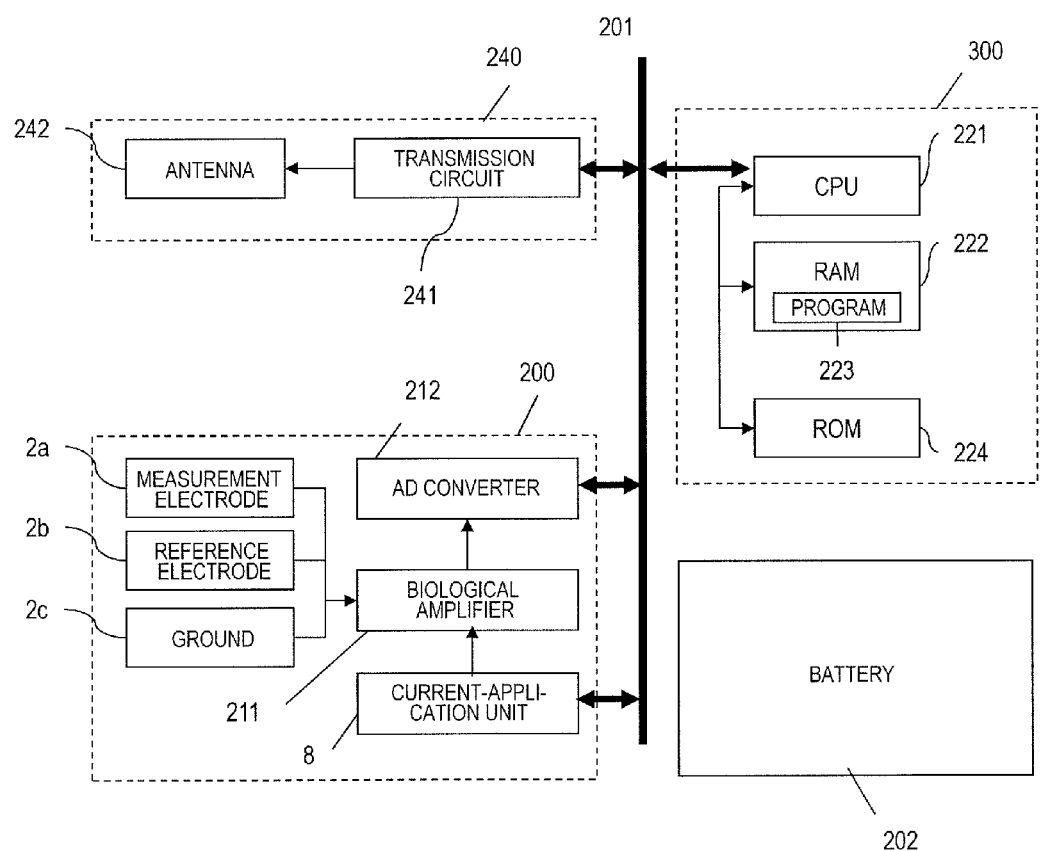
FIG. 37 is a diagram showing another exemplary hardware construction.

FIG. 37 shows another example hardware construction. In this exemplary construction, measured data is sent straightforwardly to a PC or a smartphone by a transmission section 240. The PC or smartphone having received the data will function as the data storage 6 in FIG. 36. The data transmission may occur in a wireless or wired manner.

Since the basic construction is similar to that of FIG. 36, any overlapping description concerning the biological signal measurement apparatus 200 and the biological information computation apparatus 300 will be omitted, while only the transmission section 240 will be described.

The transmission section 240 includes a transmission circuit 241 and an antenna 242. Measurement data and measurement results which have been analyzed by the biological information computation apparatus 300 are converted by the transmission circuit 241 into data formats which are suitable for the transmission protocol, and sent out at the antenna 242. The data sent from the antenna 242 is received by a receiver (not shown) which is mounted in a PC or a smartphone, and utilized in subsequent processing.

Note that, in a wireless configuration as illustrated in FIG. 37, the aforementioned signal processing such as impedance chronological data accumulation, electrocardiographic component feature detection, and envelope generation may be performed by the CPU 221 of the biological information computation apparatus 300. In other words, the CPU 221 may act as the impedance measurement unit 5, ECG component feature detector 7, envelope generator 8, respiratory output unit 9, respiratory rate estimation unit 10, respiratory volume estimation unit 11, and/or ECG component feature calibrator 12. Alternatively, without carrying out the signal processing portion, data may be first sent from the transmission section 240 to a PC or the like at the data receiving-end, and then subjected to signal processing which is performed at the receiving-end PC. When complex signal processing is performed by the signal processing section 220 in the biological signal measurement apparatus, an increase in power consumption will occur at the CPU or the like, and also power consumption is proportional to the amount of data transmission at the transmission section 240. Therefore, in order to enable monitoring over long hours, adaptations may be made to each application, concerning which one of the PC or the biological signal measurement apparatus 200 handles signal processing, and how much data is to be sent.

With the biological information recording apparatus according to the present disclosure, it is possible to measure an electrocardiogram and respiration (respiratory rate, respiratory volume) by only flowing a low current on the order of several nA, so that a biological information monitoring device can be constructed simply. Thus, both information of an electrocardiogram and respiration (respiratory rate, respiratory volume), which conventionally can only be known during hospitalization, etc., at a hospital or the like, can be assessed at one's own home, thereby enabling assessments over long hours or long periods of time. Specifically, applications are possible in fields where both heartbeats and respiration are to be measured, e.g., simplifying measurements in hospital; checking heath states at one's own home; and grasping exercise tolerance states during sports.

What is claimed is:

1. A biological information measurement system comprising:
    a plurality of electrodes provided on a thorax of a user;
    a current source electrically connected to the plurality of electrodes to supply a current to the plurality of electrodes;
    a measurement unit configured to measure impedance from a potential difference between the plurality of electrodes;
    a detector configured to detect T wave peak values of a component of electrocardiographic origin from chronological data of the impedance;
    an envelope generator processor configured to generate an impedance envelope of the T wave peak values by interconnecting T wave peaks and interpolating between the peaks to generate the envelope; and
    an output unit configured to utilize the impedance envelope to extract a respiratory component of the measured impedance to isolate the respiratory component from an electrocardiographic component of the measured impedance based on a correlation between applying the impedance envelope to the measured impedance and actual respiratory performance, and to output information of the respiratory component isolated from the electrocardiographic component as biological information concerning respiration of the user.

2. The biological information measurement system of claim 1, wherein, the impedance measured by the measurement unit contains a component of electrocardiographic origin and a component of respiratory origin; and in the impedance, the component of electrocardiographic origin is greater than the component of respiratory origin.

3. The biological information measurement system of claim 2, wherein the current source supplies a current of not less than 1 nA and not more than 107.62 µA.

4. The biological information measurement system of claim 1, wherein the current source supplies a current smaller than 350 µA.

5. The biological information measurement system of claim 1, wherein the detector detects each T wave peak value by using a value of a peak in chronological data of the impedance, and a period of time from a point in time of reaching the peak until a point in time of returning to a predetermined baseline.

6. The biological information measurement system of claim 1, wherein the detector detects R wave peaks of a component of electrocardiographic origin, and determines a peak of largest amplitude that is contained between adjacent R wave peaks as a T wave peak.

7. The biological information measurement system of claim 1, wherein the envelope generator interpolates between detected T wave peaks with a spline curve to generate an envelope.

8. The biological information measurement system of claim 1, further comprising a respiratory rate estimation unit configured to estimate a respiratory rate from information of the respiratory component output by the output unit.

9. The biological information measurement system of claim 8, wherein the respiratory rate estimation unit calculates a last period of the respiratory component by using local maximums or local minimums during estimation, and estimates the respiratory rate by using the last period.

10. The biological information measurement system of claim 9, wherein the respiratory rate estimation unit estimates a respiratory rate at every fixed time interval.

11. The biological information measurement system of claim 9, wherein, when a last amplitude of the respiratory component is equal to or less than a specific threshold value, the respiratory rate estimation unit detects suspended respiration and estimates the respiratory rate to be zero.

12. The biological information measurement system of claim 1, further comprising a respiratory volume estimation unit configured to estimate a respiratory volume from information of the respiratory component output by the output unit.

13. The biological information measurement system of claim 12, wherein the respiratory volume estimation unit estimates a respiratory volume at every fixed time interval.

14. The biological information measurement system of claim 12, wherein the respiratory volume estimation unit estimates the respiratory volume per cycle based on the level of a last amplitude of the respiratory component.

15. The biological information measurement system of claim 12, wherein the respiratory volume estimation unit detects suspended respiration when a last amplitude of the respiratory component is equal to or less than a specific threshold value during estimation, and estimates the respiratory volume to be zero.

16. The biological information measurement system of claim 1, further comprising a calibrator configured to, when a value of a specific peak of an electrocardiographic component detected by the detector is smaller than a predetermined threshold value, calibrate the value of the specific peak.

17. The biological information measurement system of claim 16, wherein the calibrator determines a last period in the respiratory component from specific peaks at previous points in time, and, as a calibration value, inputs a value of a specific peak that stands closest to a point in time obtained by subtracting the last period from a point in time of the specific peak which is smaller than the predetermined threshold value, into the value of the specific peak which is smaller than the predetermined threshold value.

18. A biological information computation apparatus comprising:

a detector configured to receive chronological data of impedance which is measured from a potential difference between a plurality of electrodes provided on a thorax of a user by using a current supplied from a current source, and detect T wave peak values of a component of electrocardiographic origin from the chronological data;

an envelope generator processor configured to generate an impedance envelope of the T wave peak values by interconnecting T wave peaks and interpolating between the peaks to generate the envelope; and an output unit configured to utilize the impedance envelope to extract a respiratory component of the measured impedance to isolate the respiratory component from an electrocardiographic component of the measured impedance based on a correlation between applying the impedance envelope to the measured impedance and actual respiratory performance, and to output information of the respiratory component isolated from the electrocardiographic component as biological information concerning respiration of the user.

19. A biological information measurement method comprising:

supplying a current to a plurality of electrodes provided on a thorax of a user;

measuring impedance from a potential difference between the plurality of electrodes;

from chronological data of the impedance, detecting T wave peak values of a component of electrocardiographic origin;

generating an impedance envelope of the T wave peak values by interconnecting T wave peaks and interpolating between the peaks to generate the envelope; and utilizing the impedance envelope to extract a respiratory component of the measured impedance to isolate the respiratory component from an electrocardiographic component of the measured impedance based on a correlation between applying the impedance envelope to the measured impedance and actual respiratory performance, and outputting information of the respiratory component isolated from the electrocardiographic component as biological information concerning respiration of the user.

20. A non-transitory computer-readable medium storing a computer program to be executed by a computer provided in a biological information measurement system, the computer program causing the computer to execute:

receiving chronological data of impedance which is measured from a potential difference between a plurality of electrodes provided on a thorax of a user by using a current supplied from a current source;

detecting T wave peak values of a component of electrocardiographic origin from the chronological data;

generating an impedance envelope of the T wave peak values by interconnecting T wave peaks and interpolating between the peaks to generate the envelope; and utilizing the impedance envelope to extract a respiratory component of the measured impedance to isolate the respiratory component from an electrocardiographic component of the measured impedance based on a correlation between applying the impedance envelope to the measured impedance and actual respiratory performance, and outputting information of the respiratory component isolated from the electrocardiographic component as biological information concerning respiration of the user.

* * * * *